(12) United States Patent
Reed

(10) Patent No.: US 8,322,199 B2
(45) Date of Patent: Dec. 4, 2012

(54) AUTOMATIC SAMPLING AND DILUTION APPARATUS FOR USE IN A POLYMER ANALYSIS SYSTEM

(75) Inventor: Wayne F. Reed, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 956 days.

(21) Appl. No.: 11/706,458

(22) Filed: Feb. 14, 2007

(65) Prior Publication Data

US 2008/0008623 A1 Jan. 10, 2008

Related U.S. Application Data

(63) Continuation of application No. 10/442,676, filed on May 21, 2003, now abandoned.

(60) Provisional application No. 60/382,213, filed on May 21, 2002.

(51) Int. Cl.
*G01N 1/00* (2006.01)

(52) U.S. Cl. ....... 73/64.56; 422/130; 422/131; 422/501; 422/509

(58) Field of Classification Search .................. 422/68.1, 422/100, 101, 102, 129, 130, 131, 501, 509; 436/52, 164, 174, 179, 180; 73/54.01, 54.02, 73/64.54, 863.01, 863.02, 64.56

See application file for complete search history.

(56) References Cited

U.S. PATENT DOCUMENTS

| | | |
|---|---|---|
| 3,607,082 A | 9/1971 | Thiers |
| 4,100,142 A | 7/1978 | Schaefer et al. |
| 4,105,137 A | 8/1978 | Bemet et al. |
| 4,204,430 A | 5/1980 | Tamm et al. |
| 4,258,564 A | 3/1981 | Hulme et al. |
| 4,274,749 A | 6/1981 | Lake et al. |
| 4,375,524 A | 3/1983 | Rowe |
| 4,422,036 A | 12/1983 | Moll et al. |

(Continued)

FOREIGN PATENT DOCUMENTS

FR 002579749 A1 10/1986

(Continued)

OTHER PUBLICATIONS

Liquid Pumps—Viscosity Handling Characteristics, Nov. 14, 2001 http://www.coleparmer.com/techinfo/techinfo.asp?htmlfile=P_ViscosityHandling.htm.

(Continued)

*Primary Examiner* — Jill Warden
*Assistant Examiner* — Dwayne K Handy
(74) *Attorney, Agent, or Firm* — Olson & Cepuritis, Ltd.

(57) ABSTRACT

The present invention provides an automatic sampling and dilution apparatus for use in a polymer analysis system. The apparatus comprises (a) a primary mixing chamber; (b) a primary pump capable of continuously withdrawing a variable viscosity liquid from a reactor at a selectable, fixed withdrawal rate over a varying viscosity range of about 50 to about 5,000,000 centipoise (cP) for continuously conveying the variable viscosity polymer-containing liquid into the primary mixing chamber; (c) a first dilution pump for continuously delivering a first dilution solvent into the primary mixing chamber at a selectable, fixed flow rate to mix with the variable viscosity liquid in the mixing chamber and thereby form a diluted polymer-containing liquid therein; and (d) a secondary pump for continuously conveying the diluted polymer-containing liquid into a flow-through detector. A polymer analysis system utilizing the automatic sampling and dilution apparatus is also provided.

35 Claims, 17 Drawing Sheets

U.S. PATENT DOCUMENTS

| | | | |
|---|---|---|---|
| 4,495,028 A | 1/1985 | Rowe | |
| 4,686,086 A | 8/1987 | Rowe | |
| 4,794,806 A | 1/1989 | Nicoliu et al. | |
| 4,804,519 A | 2/1989 | Sainz | |
| 4,826,775 A | 5/1989 | Burns et al. | |
| 5,439,992 A | 8/1995 | Yi et al. | |
| 5,483,013 A | 1/1996 | Roth et al. | |
| 5,705,572 A | 1/1998 | Yi et al. | |
| 5,728,793 A | 3/1998 | Kumagai et al. | |
| 5,744,555 A | 4/1998 | Ames et al. | |
| 5,907,108 A | 5/1999 | Garcia-Rubio et al. | |
| 6,052,184 A | 4/2000 | Reed | |
| 6,160,060 A | 12/2000 | Hilliday et al. | |
| 6,175,409 B1 * | 1/2001 | Nielsen et al. | 506/12 |
| 6,880,966 B1 * | 4/2005 | Cappellino et al. | 366/171.1 |

FOREIGN PATENT DOCUMENTS

| | | |
|---|---|---|
| GB | 2090814 A | 7/1982 |
| GB | 2294761 A | 5/1996 |
| JP | 53007576 A | 1/1978 |
| JP | 56097508 A | 8/1981 |
| JP | 358037559 A | 3/1983 |
| JP | 60187863 | 9/1985 |
| JP | 08196883 A | 1/1995 |

OTHER PUBLICATIONS

Chemical and Pharmaceutical Plants. Thin-Film Processor KONTRO, http://www.pi.hitachi.co.jp/sanpue/Equipment/2010588__17436.html, the date on-line is unknown.

* cited by examiner

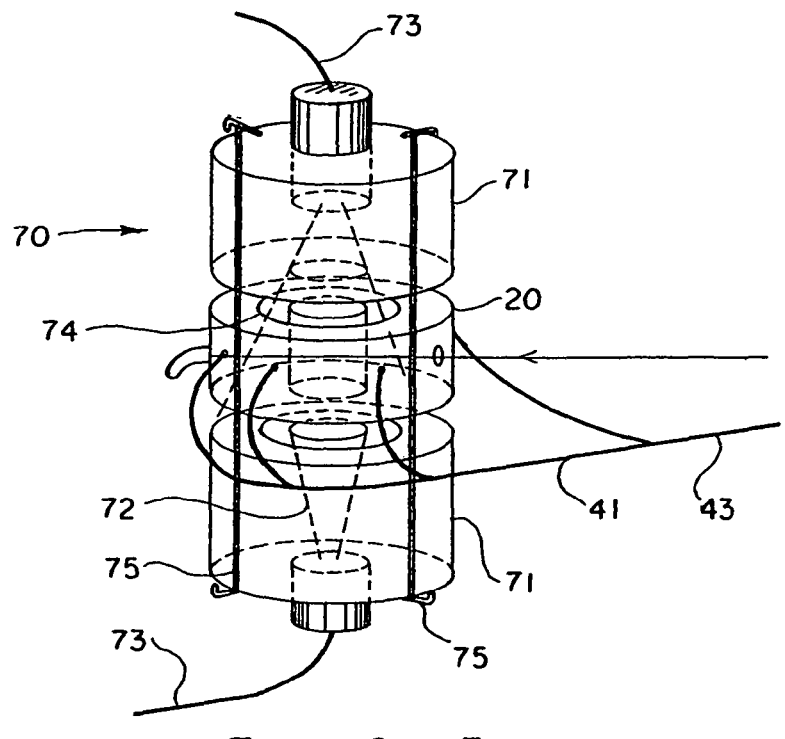
F I G. 3
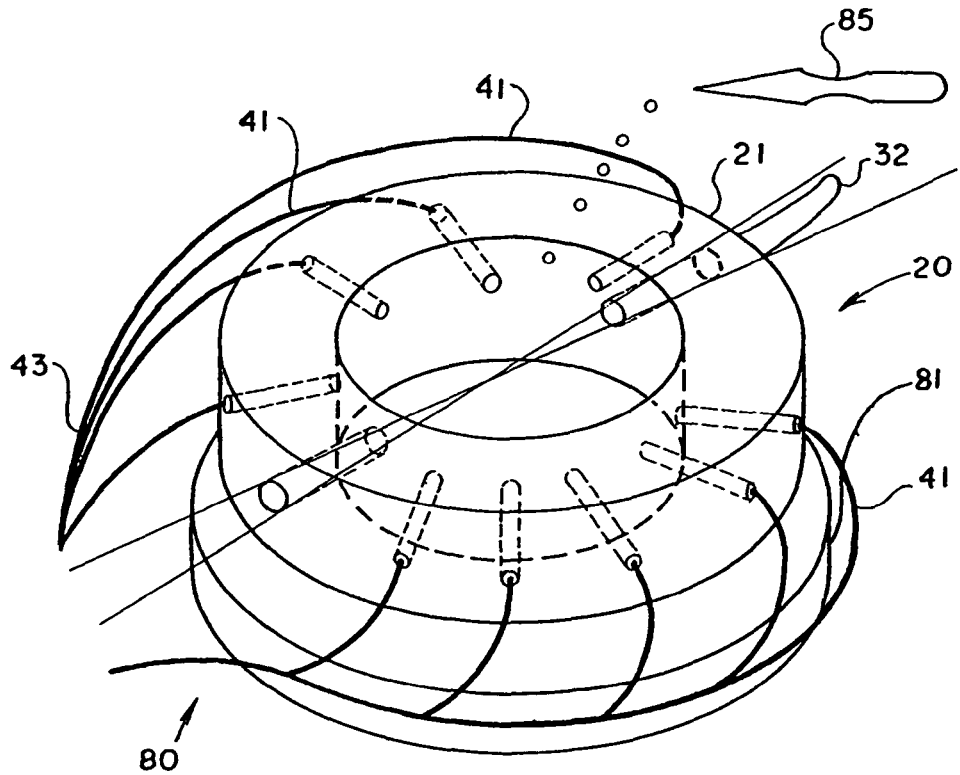
F I G. 4

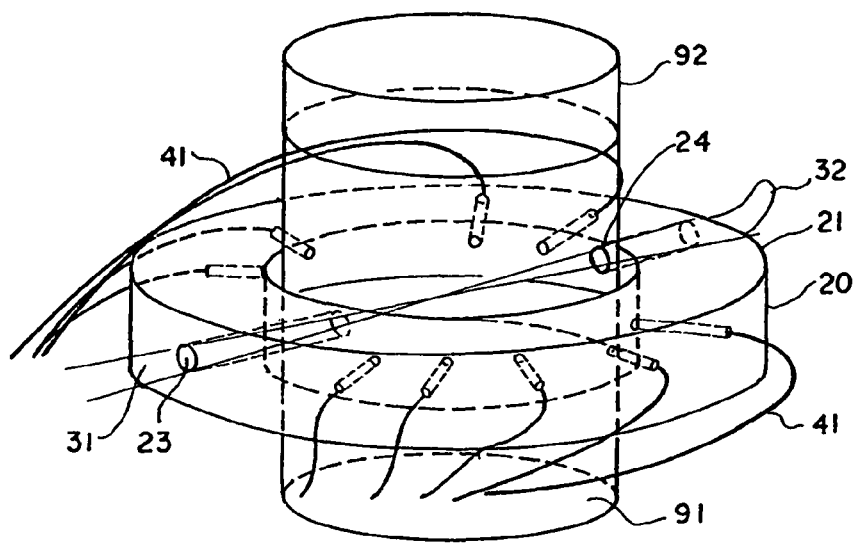
F I G. 5
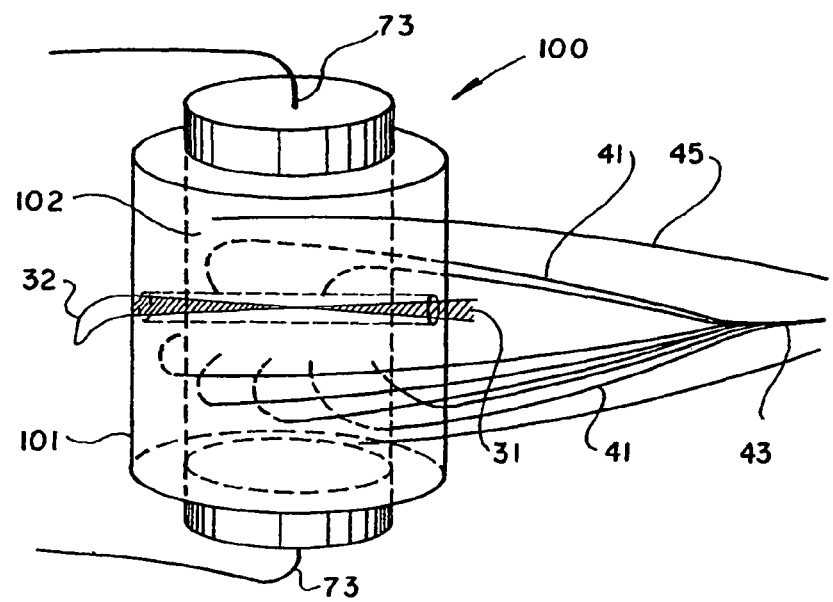
F I G. 6

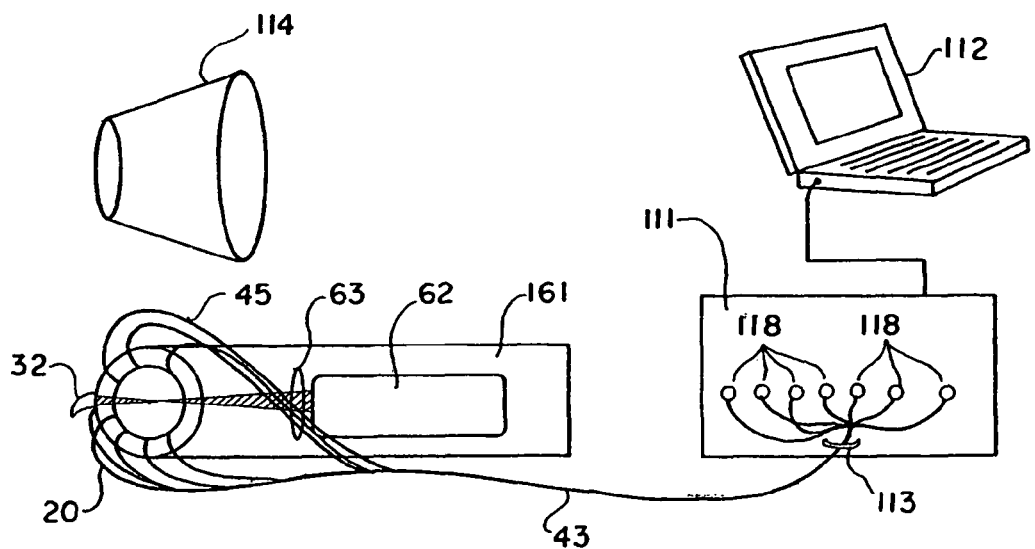
F I G . 7
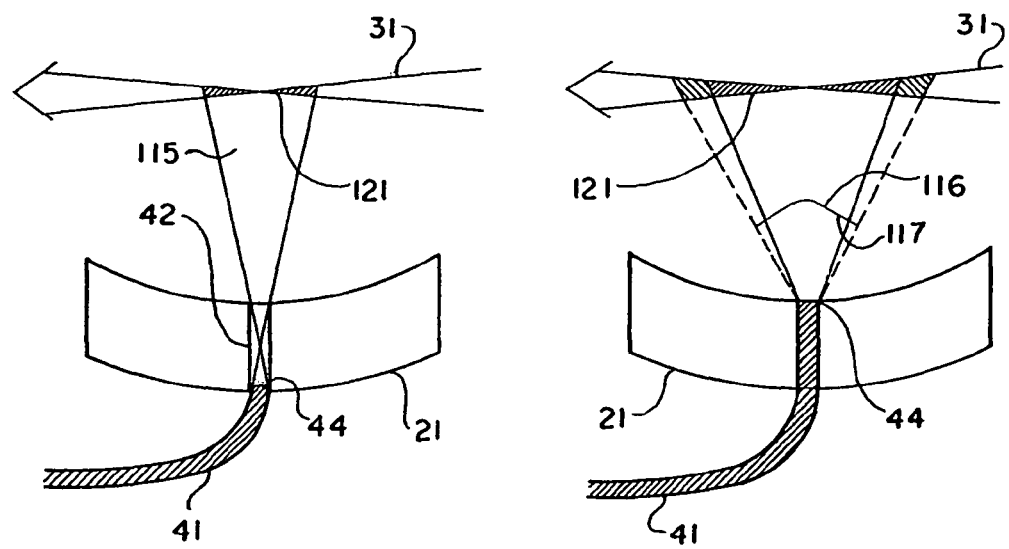
F I G . 8       F I G . 9

AUTOMATIC SAMPLING AND DILUTION APPARATUS FOR USE IN A POLYMER ANALYSIS SYSTEM

CROSS-REFERENCE TO RELATED APPLICATIONS

This application is a continuation of U.S. application patent Ser. No. 10/442,676, filed on May 21, 2003, now abandoned which claims the benefit of U.S. Provisional Application Ser. No. 60/382,213, filed on May 21, 2002, both of which are incorporated herein by reference.

STATEMENT OF GOVERNMENT INTEREST

This invention was made with U.S. government support under Grant No. CTS0124006, awarded by the National Science Foundation. The US government has certain rights in this application.

BACKGROUND OF THE INVENTION

1. Field of the Invention

The present invention relates to the absolute characterization of microscopic particles in solution. More particularly, the present invention relates to the absolute characterization of microscopic particles, such as polymers and colloids using static light scattering (SLS) and time-dependent static light scattering (TDSLS). In principle, the size range of detectability should run from about 20 Angstroms to 100 microns, with useful measurability in the range from 20 Angstroms to 2 microns, and a preferred range from about 20 Angstroms to 5000 Angstroms. Stated in terms of molar mass, the detectable range of particles should run from about 500 g/mole to $10^{14}$ g/mole, with useful measurability in the range of 500 g/mole to $10^9$ g/mole, with a preferred range from about 1000 g/mole to $10^7$ g/mole.

The preferred use of this invention is the determination of average particle masses, static dimensions, interaction coefficients, and other properties, as well as their changes in time, when scattering is from a very large number of particles. This is to be distinguished from turbidometric and nephelometric techniques, in which turbidity or relative scattering of solutions is measured and compared to relative reference solutions, in order to obtain concentrations of particles. The SLS technique employed refers to absolute macromolecular characterization, and not to determinations of concentrations of particulates with respect to specific relative calibrations, etc. This is also to be distinguished from devices which count and characterize single particles, although the present invention can count and characterize single particles, in addition to making SLS measurements. The least number of particles whose scattered light would be detected in the scattering volume (the volume of illuminated sample whose scattering is measured by a given photodetector) would be on the order of 20 and the maximum on the order of $4\times10^{17}$, with the preferred range being from about 15,000 to $1.5\times10^{13}$ particles. In terms of concentration of solute (dissolved polymer or colloid) the range would be from about $10^{-8}$ g/cm$^3$ (for very large particles) to 0.2 g/cm$^3$ (for very small particles) with the preferred range being from about $10^{-6}$ to $10^{-1}$ g/cm$^3$. It should be pointed out that SLS in the absolute mode requires optically transparent solutions in which single, not multiple, scattering dominates. Many particle concentration detectors actually work in turbid solutions, which is a different range of conditions entirely.

SLS has proven to be a useful technique not only for characterizing equilibrium properties of microscopic particles, such as molar mass, dimensions and interactions, but also for following time-dependent processes such as polymerization, degradation and aggregation. Measuring the time-independent angular distribution and absolute intensity of scattered light in the equilibrium cases allows the former properties to be determined, according to procedures set forth by Lord Rayleigh, Debye, Zimm and others (e.g. ref. 1). In particular, this invention can be used in conjunction with the well known procedure of Zimm to determine weight average molar mass $M_w$, z-average mean square radius of gyration $<S^2>_z$ and second virial coefficient $A_2$. Measuring the time-dependent changes in the scattered intensity allows calculation of kinetic rate constants, as well as deduction of kinetic mechanisms and particle structural features (e.g. refs. 2,3). TDSLS can be used to monitor polymerization and degradation reactions, aggregation, gelling and phase separation phenomena (e.g. ref. 4).

In addition to absolute SLS and TDSLS measurements, the present invention can also simultaneously count and characterize individual particles which are much larger than the principal polymer or colloid particles; e.g., the large particles may have a radius of 5 microns, whereas the polymer may have an effective radius of 0.1 micron. The large particles may represent a contaminant or impurity, or may be an integral part of the solution, e.g., bacteria (large particles) produce a desired polymer (e.g., a polysaccharide) in a biotechnology reactor. The number density of bacteria can be followed in time, and the absolute macromolecular characterization of the polysaccharide could also be made (an auxiliary concentration detector would also be necessary if the polysaccharide concentration changes in time).

The present invention involves automatic online mixing and/or dilution of solutions containing polymers and/or colloids in order to provide relative and/or absolute characterization of these microscopic particles in solution. In the following, the term 'dilution' will be used, because, whenever two or more solutions are mixed, as described herein, the solutes in each will become dilute. The automatic dilution is intended to replace the traditional prior art of manually diluting such polymer/colloid solutions in order to make characterizing measurements, and to extend measurement capabilities to novel situations, especially those involving non-equilibrium (that is, time-dependent) processes, such as polymerization, degradation, aggregation and phase separation. The method can be used in conjunction with a variety of detectors, such as static light scattering (SLS), time-dependent static light scattering (TDSLS), heterogeneous time dependent light scattering (HTDSLS), dynamic light scattering, refractometry, ultraviolet and visible spectrophotometry, turbidometry, nephelometry, viscometry and evaporative light scattering. The automatic, online dilution of polymer and/or colloid solutions will be shown to have broad applicability in many sectors. In referring to the ensemble of SLS, TDSLS and HTDSLS detectors and methods in the following, the term light scattering (LS) will be used for brevity.

In principle, the size range of detectability of the polymers and/or colloids should run from about 20 Angstroms to 100 microns, with useful measurability in the range from 20 Angstroms to 20 microns, and a preferred range from about 20 Angstroms to 5000 Angstroms. Stated in terms of molar mass, the detectable range of particle molar masses should run from about 500 g/mole to 1014 g/mole, with useful measurability in the range of 500 g/mole to 1011 g/mole, with a preferred range from about 1000 g/mole to 1010 g/mole.

This invention focuses on automated methods that are used to characterize equilibrium and non-equilibrium properties of solutions containing polymers and/or colloid particles. Characterization of polymers and colloids via LS detectors is in terms of average particle masses, static dimensions, interaction coefficients, and other properties, as well as their changes in time, when scattering is from a very large number of particles. When large colloidal particles are present, the use of the method in conjunction with HTDSLS also allows the determination of the number density of these particles, information on their dimensions, and, when the system is not in equilibrium, how these properties change in time.

SLS has proven to be a useful technique for characterizing equilibrium properties of microscopic particles, such as molar mass, dimensions and interactions, and TDSLS and HTDSLS for following time-dependent processes such as polymerization, degradation and aggregation. Measuring the time-independent angular distribution and absolute intensity of scattered light in the equilibrium cases allows the former properties to be determined, according to procedures set forth by Lord Rayleigh, Debye, Zimm and others (e.g. ref. 1). In particular, this invention can be used in conjunction with the well known procedure of Zimm to determine weight average molar mass Mw, z-average mean square radius of gyration $<S2>z$ and second virial coefficient A2. Measuring the time-dependent changes in the scattered intensity allows calculation of kinetic rate constants, as well as deduction of kinetic mechanisms and particle structural features (e.g. refs. 2,3). TDSLS can be used to monitor polymerization and degradation reactions, aggregation, gelling and phase separation phenomena (e.g. ref. 4).

In addition to absolute SLS and TDSLS measurements, use of the present invention in conjunction with HTDSLS allows simultaneous counting and characterization of individual particles which are much larger than the principal polymer or colloid particles; e.g., the large particles may have a radius of 5 microns, whereas the polymer may have an effective radius of 0.1 micron. The large particles may represent a contaminant or an impurity, or may be an integral part of the solution, e.g., bacteria (large particles) produce a desired polymer (e.g., a polysaccharide) in a biotechnology reactor. The number density of bacteria can be followed in time, and the absolute macromolecular characterization of the polysaccharide could also be made (an auxiliary concentration detector would also be useful if the polysaccharide concentration changes in time).

The method whereby simultaneous, absolute characterization of polymers and number counting of large particles is carried out, is described in U.S. patent application Ser. No. 08/969,386 (now U.S. Pat. No. 6,052,184). To optimize the technique, one should make the sample liquid flow relative to the irradiating laser beam (or other light source) in the scattering chamber, so as to produce countable scattering spikes as each large particle passes through the detected portion of the illuminated volume (the 'scattering volume'), while ensuring, via correct design of the optical and electronic detection system, that there is on the average less than one large particle in the scattering volume at any given time. This allows the scattering level to recover to the baseline scattering of the pure polymer between the scattering spikes due to the large particles, so that the polymer can be absolutely characterized. The fraction of baseline time termed herein 'clear window time', and is detailed mathematically in ref. 5, wherein the method has recently been demonstrated. In this demonstration, it was first shown that useful characterization of a polymer solution could be made even in the presence of a large amount of particulate contamination. The contaminant was a known amount of 2 micron latex spheres introduced in increasing amounts to an aqueous polymer solution containing the polymer poly(vinyl pyrrolidone), or PVP. Secondly, the ability to simultaneously make absolute characterization of the polymer while the change in time of the large particle population was monitored was demonstrated by monitoring the growth of *E. Coli* bacteria amidst an aqueous solution of PVP polymer.

The present invention also involves the automatic extraction and dilution of high viscosity fluids.

More particularly, the present invention also includes a device for automatically and continuously sampling and diluting liquids of high viscosity, normally containing synthetic and/or biological polymers, to such an extent that absolute light scattering and/or other optical and physical measurements can be made. In many cases the viscosity in the vessel containing the fluid will vary continuously from a low value to a high value (polymerization reaction), or vice versa (degradation or phase separation reaction). In some instances it will be desirable to manually or automatically change the dilution factor during the course of a reaction or monitoring process.

2. General Background of the Invention

There is currently considerable interest in the polymer industry for finding a means of monitoring and controlling, in real-time or near real-time, the progress of polymerization and other reactions. Here, 'polymer industry' is understood to mean all industries producing synthetic polymers (e.g. polyolefins), as well as those producing or modifying biological or bioactive polymers, whether for food, pharmaceutical, cosmetic, or other applications. 'Polymer reaction' is understood to mean polymerization, copolymerization, degradation, or any means of modifying the chemical or physical properties of polymers.

Currently, the state of the polymer reaction can be found by manually sampling the reactor and making any number of analytical tests on the contents. This, however, leads to long delay times in obtaining results, usually too long to make useful adjustments to the reaction. Often times the analytical laboratory facilities are located remotely from the reactor. Such manual sampling also does not yield a continuous enough record of the reaction to follow the time course quantitatively. There can also be safety issues involved when workers expose themselves to hazardous reactor environments to obtain samples.

A step towards automation has been proposed recently by Symyx Technologies, Inc. (Ca.) and others, wherein a discrete, automatic sampling of reactor contents occurs, followed by injection of a finite volume of the extracted material into an analytical system, which contains a series of detectors, and, optionally, a chromatographic column to perform some separation of the injected material. This type of procedure leads to signal peaks in the detectors each time a sample is injected. The peaks are then normally analyzed using standard analytical practice to obtain molecular masses, degree of monomer conversion, and, sometimes, reduced viscosity. The actual sampling and dilution is normally carried out by a robotic system. For example, Waters introduced such an auto sampling system. All these techniques involve injection of a material to produce peaks, and yield data points separated by significant dead-times, during which the sampling and detector system recover in preparation for the next injected pulse of material. These techniques, including the manual one, can be termed 'discrete sampling' techniques.

The current invention builds off of an alternative sampling and analysis method, previously introduced by this inventor. This method is a continuous one, and does not involve injecting pulses of material and subsequently obtaining detector peaks for analysis. Recently, the inventor has coined the term Automatic, Continuous, Online Monitoring of Polymerization Reactions (ACOMP) for this method. In ACOMP a stream of material from the reactor is continuously mixed with a solvent, and the diluted mixture flows through the detector train, providing a continuous record of the reaction. In ACOMP no chromatographic columns are used, finite pulses of material are not injected into the detector train (although they may be injected into the mixing chamber), and detector signal peaks are not obtained. Another area of reaction monitoring involves in situ probes, such as near Infra-red and rheometers. While these probes allow real-time or near real-time data on the reaction to be gathered, they are inevitably empirical methods, largely based on chemometric approaches, which show a statistical relationship between a desired polymer property and an instrument's signal. ACOMP, in contrast, involves absolute measurements of molecular properties. ACOMP theory, practice and instrumentation, and related techniques, have been extensively described by the inventor and his co-workers. (Refs. 5, 6, 7, 8-17).

The single greatest problem in the practical use of ACOMP is the automatic, continuous preparation of the mixed or diluted sample which continuously feeds the detector train. The problem is due chiefly to the high viscosities which develop during many polymerization reactions, as well as the bubbles that can occur. Commercially available mixers are available, that use either high pressure (e.g. Dionex, Waters) or low pressure mixing schemes (e.g. Isco). The problem with these devices is that they are designed and built to handle only low viscosity liquids. When one of the feeds to a low pressure mixing pump is a reactor whose viscosity increases during a polymerization reaction, the mixing pump is incapable of maintaining a fixed volume withdrawal rate percentage. The result is that the lag time between withdrawal from the reactor and arrival of the mixed solution at the detectors becomes longer and longer as the reaction proceeds, often times to unacceptable levels. When a high pressure mixing scheme is used, bubbles produced either by the reaction itself, or due to cavitation during pump withdrawal, lead to the depriming of the withdrawal pump, and failure to continue monitoring. The check valves and other plumbing in such pumps is also susceptible to becoming frozen by plugs of polymeric material that can solidify in the pumps during operation. It is apparent that pumps that rely on pulling reactor material with a vacuum (1 atmosphere or less) are wholly unsuitable for ACOMP when viscosities are above about 150 centipoise (cP); i.e. arrangements of such pumps can typically follow a reaction from about 1 cP to about 150 cP.

On the other hand, a variety of pumps exist that can handle highly viscous materials. Certain peristaltic pumps, for example can pump liquids up to tens of thousands of cP, whereas gear, lobe and screw pumps can move liquids of millions of cP. Whereas this latter technology is highly developed for industries involving, for example, plastic injection and synthetic fiber production, there is no available system that can accomplish the prerequisite of ACOMP: Continuously withdraw a very small flow rate of material and mix it homogeneously with a solvent.

More information about the background of the inventions disclosed and claimed herein can be found in my patent applications mentioned herein.

Incorporated by reference are the following papers: Florenzano, Strelitzki and Reed, *Macromolecules*, vol. 31, pp. 7226-7238, 1998, "Absolute, On-line Monitoring of Molar Mass during Polymerization Reactions"; Strelitzki and Reed, *Journal of Applied Polymer Science*, vol. 73, pp. 2359-2368, 1999, "Automated Batch Characterization of Polymer Solutions by Static Light Scattering and Viscometry"; Schimanowski, Strelitzki, Mullin, and Reed, "Heterogeneous Time Dependent Static Light Scattering", *Macromolecules*, (copy attached to U.S. patent application Ser. No. 09/404,484).

SUMMARY OF THE INVENTION

The present invention is the first fully submersible SLS probe for absolute macromolecular characterization (as opposed to particle counting, nephelometry, dynamic light scattering, or relative concentration measurements). The optical assembly of the present invention can be completely immersed in the scattering medium. Thus, the present invention includes a scattering probe which can 'go into' the medium to be measured (e.g. into test tubes, production vats, etc.), and samples of the scattering medium need not be introduced into a transparent sample cell remote from the medium itself, as is done in current systems. In the present invention the probe can be submerged in a variety of harsh environments, as concerns temperature, pressure and solvents, and communicates to the remote electronic and signal processing portion via a harness containing fiber optic cables.

The present invention can be used in several distinct modes (immersion, fill mode, insert mode and flow mode), giving it wide versatility. The probe of the present invention is not constrained to be immersed in order to function. A small quantity of sample can also be placed in the optical assembly compartment for measurement in a 'fill mode'. A sample in a transparent vial or cell can also be placed in the chamber or ring member for measurement. Also, the probe can be hooked into a flowing stream of sample liquid for use in different applications such as polymer separation (e.g. size exclusion chromatography), and on-line, unfractionated flows of polymers in a vessel in equilibrium, or undergoing polymerization, aggregation, cross-linking or degradation processes.

The present invention can respond to the needs of a wide variety of users and applications by simply changing the inexpensive optical assembly, since the detection, electronics, computer interfacing and basic software are all the same. For example, a miniature probe with a 10 microliter channel could plug into the same 'detection/analysis' back-end as a 50 milliliter optical probe designed for immersion at high temperatures. There is wide room for substitution of different diameter fibers with different acceptance angles, number of photodetectors on the 'detection/analysis' back-end, etc.

The present invention does not require a transparent sample cell for the scattering solution. Unlike all current SLS systems for absolute macromolecular and colloidal characterization, no glass or other transparent cell need intervene between the sample, the detection fibers and the fiber or lens used for introducing the incident beam. Major advantages which this confers includes avoiding the expense, maintenance and cleaning of transparent cells, and minimizing glare and stray light, because the optical assembly is preferably made from a very dark or black material, and hence does not have highly reflective glass and/or other dielectric surfaces causing spurious glare and reflections.

The optical probe portion of the present invention is preferably miniature in scale. Whereas other devices also use only small sample volumes, those devices require that the sample be pumped or injected in through appropriate plumbing. In the present invention, when used in the fill mode, small quantities of sample can be simply pipetted or dropped into the optical assembly compartment, where they reside during the measurement.

The probe can achieve both absolute calibration and self-cleaning simultaneously when immersed in a proper solvent, such as toluene. Furthermore, because of the direct immersion there are no problems with index of refraction corrections associated with cells which do not maintain cylindrical symmetry about an axis perpendicular to the scattering plane. Hence, well-known, non-proprietary standard calibration procedures can be used for each detector.

The versatile scattering chamber is very inexpensive to fabricate and, in some instances, can be even treated as disposable. This contrasts to the generally high cost of the scattering cell/detector assembly in prior art units.

Unlike existing SLS units, the use of fiber optic detectors and narrow beam focusing make the system quite insensitive to alignment. This has the significant advantage of allowing the unit to operate with a simple coarse alignment, whereas a high degree of alignment is normally required in existing systems. This is achieved because the acceptance cone of the fibers is fairly large (typically 9°) and the beam is collimated to usually less than 100 microns. Hence, at a remove of 3 mm from the fiber, the beam can be moved up and down approximately 0.5 mm for a 9° acceptance angle fiber, without significantly changing the amount of scattered light entering the fiber.

Properly minimizing the scattering volume with a focused beam and using fiber optic detectors and fast detection electronics allow unfiltered samples to be measured, even when no flow or other relative motion between sample and detector exists. This is a major advance, considering that SLS in conventional instruments only became reliable after chemical filtration technologies improved considerably.

The present invention includes a submersible device, which measures relative light scattered at various angles from a large number of scattering particles, from which absolute macromolecular and colloidal characterization is made, via well known, non-proprietary calibration procedures and the well known procedures of Zimm and others. The device need not contain an optically transparent cell interposed between the scattering medium and the incident optic delivering the incident beam and the optical fibers used for detection.

The submersible absolute macromolecular characterization device described in the previous paragraph preferably consists of a completely solid or perforated, or striated or otherwise partially open solid piece, a ring member or a cylinder with a channel inside into which sample liquid enters upon immersion. In this device, polarized or unpolarized incident light (provided by a laser or any other source of visible or ultraviolet light) is led into the channel and spatially filtered with any suitable optical elements such as a tubular lens, miniature convex lens, flat window, fiber optic, irises, etc., or any suitable combination. The light so led in can undergo any necessary degree of collimation, including none, in order to make as narrow an incident beam waist in the detected scattering volume as desired. Scattered light detection is preferably achieved by fiber optic strands, or other fiber optic light conduits, which are exposed to scattered light in the channel, either by virtue of being recessed into the walls of the channel, being flush with the walls of the channel, or protruding into the channel. The degree of collimation of incident light and the diameter of the detecting fibers are combined to optimize the detected scattering volume for the particular sample to be measured. The transmitted incident light is preferably 'dumped' using any standard beam dump arrangement, such as a hole, Rayleigh horn, prism, etc. The channel is preferably black or blackened to reduce glare and stray light from the incident beam. The delivery and detection optical train elements are preferably gathered into a harness leading to the photodetectors, amplifiers and computer external to the light scattering probe.

Instead of the probe mentioned above which can be immersed in sampling liquid, a different probe can be provided, into whose channel, plugged at one end, rather, a small quantity of sample liquid can be transferred (e.g. by pipette, or by scooping) and therein reside while the scattering measurements are made.

Likewise, a third probe having suitable liquid flow connectors need not be immersed in sampling liquid; instead, through its channel the sample liquid can be made to flow for scattering measurements.

The submersible absolute macromolecular characterization device described above can consist of a ring member, not necessarily closed or circular (e.g. rectangular, elliptical, horseshoe, or any other shape capable of holding the light source fixed relative to the detection fibers (or photodetector when detection fibers are not used)) containing the incident beam delivery optics, beam dump and detection fibers, and which can be immersed directly in a sample liquid for scattering measurements. Alternatively, the submersible absolute macromolecular characterization device described above can consist of a ring member, not necessarily closed or circular (e.g. rectangular, elliptical, horseshoe, etc.) which can be placed inside of a chamber in a cell of appropriate dimension, so as to protect it from the liquid it is immersed in, ambient light or other factors, or to otherwise control how sample liquid reaches the ring member for scattering measurements.

The present invention includes a method whereby any of the devices described above, with appropriately small scattering volume, can be used to measure sample solutions which may contain significant numbers of large scattering contaminants by using fast enough photodetector response to identify, count and eliminate scattering intensity spikes produced by the contaminants, thereby enabling the recovery of the uniform scattering background due to the population of polymers or colloids in the sample. The sample may be either stationary or flowing to accomplish this. Very roughly, the number density of contaminant particles can be on the order of one per scattering volume, so that very tiny scattering volumes allow for relatively higher concentrations of impurity to be present. The identified spikes can be counted and used to assess the particle density of large particles in a solution, and how this number may change in time, as well as simultaneously determining the absolute uniform scattering from a population of polymer or colloids.

The present invention also includes a method whereby the flow mode of the present invention described herein can be used to measure, in real-time, the increase of the weight average molecular weight of polymers being produced in a solution of chemicals undergoing polymerization reactions. This method preferably includes the on-line dilution of the polymer containing solution to bring it into a concentration range where useful, absolute scattering can be measured. This range is where the quantity $2A_2 cM_w$ is preferably smaller than 1, but can actually be as much as 10. Such dilution can be achieved by the use of hydraulically pulling polymer solution and pure solvent through an hydraulic 'T' or other mixing chamber via a pump or other flow-causing device. A concentration sensitive detector is preferably installed in the line of fluid flow so as to determine in real-time the actual concentration of polymer in the diluted solution. Such a detector may be a refractive index monitor, ultraviolet or visible spectrophotometer, etc.

The present invention also includes a method whereby any of the devices herein described are used to monitor the changes in time of polymer solutions which are undergoing degradation, polymerization, aggregation, gelling, or phase separation.

The present invention also includes a method whereby any of the devices herein described are used to usefully characterize heterogeneous solutions, containing populations of both polymers or colloids and large particulate scatterers, whether either or both of these changes in time or not.

The present invention comprises a kit including light scattering devices of the type described herein, whereby a wide variety of optical probes (with widely varying dimensions, sample capacities, fiber optic types, numbers of angles) made of different materials to withstand different environments can be connected to the same 'back-end' of detection electronics, signal processing and data analysis. The kit can also include the detection electronics, signal processing and data analysis.

The present invention also includes a submersible light scattering probe for the absolute characterization of polymer and colloid solutions which includes a ring member made of a preferably dark, opaque material, having embedded therein a plurality of optical fibers which can be connected to optical detectors remote from the probe. The ends of the optical fibers are preferably in direct contact with the fluid being tested. Instead of submersing the probe in a fluid, fluid can be caused to flow through the probe, placed in the probe, or placed in a transparent vessel placed in the probe. Individual large scattering particles can also be detected, counted, and characterized at the same time absolute characterization of the polymer or colloid solution is performed.

This method preferably includes the on-line dilution of the polymer-containing solution to bring it into a concentration range where useful, absolute scattering can be measured. This range is where the quantity 2A2cMw is preferably smaller than 1, but can actually be as much as around 10 (or even higher). Such dilution can be achieved by the use of hydraulically pulling polymer solution and pure solvent through an hydraulic 'T' or other mixing chamber via a pump or other flow-causing device. A concentration sensitive detector is preferably installed in the line of fluid flow so as to determine in real-time the actual concentration of polymer in the diluted solution. Such a detector may be a refractive index monitor, ultraviolet or visible spectrophotometer, etc.

FIG. 16 illustrates the scheme used by the inventor et al. (Ref. 6) for the online monitoring of a poly(vinyl pyrrolidone), or PVP, reaction.

The present invention also includes a method whereby heterogeneous solutions, containing populations of both polymers or colloids and large particulate scatterers, can be characterized, whether either or both of these changes in time or not.

FIG. 17 shows a three vessel scheme, wherein one vessel contains the polymer or colloid to be characterized, and two other vessels are used, each of which contains different solvents. For example, the polymer might be electrically charged (i.e. a polyelectrolyte) and be dissolved in pure water in the first vessel, whereas solvent #1 might be pure water, and solvent #2 an aqueous solution containing salt. With such an arrangement it would be possible to maintain a fixed polymer concentration by pulling a fixed fraction from the first vessel, while the total salt concentration that the polyelectrolyte is subjected to is continuously changed from pure to very salty water (e.g. 4 molar NaCl). Since the concentration of polyelectrolyte is fixed, and known, a LS detector alone would furnish online information on how the polyelectrolyte conformations and interactions are changing as the solvent becomes more salty. Adding a viscometer would further indicate how the polyelectrolyte hydrodynamic properties are changing with salt concentration.

Similarly, other types of polymers and/or colloids could be in the first vessel, and solvent #1 could be of one type (e.g. pure water) and solvent #2 could be of another type (e.g. an alcohol or other solvent miscible in water). In this way the effects of changing solvent composition on the polymer and/or colloid could be continuously assessed online. Many other variations are possible, since the second solvent could also contain a polymer and/or colloid which interacts with the first polymer and/or colloid solution. The three vessel arrangement hence allows complete phase diagrams to be obtained online. Another area of use would be to determine under what solvent conditions globular polymers, such as proteins, become denatured into random coils.

Extension to more than three vessels is straightforward and is contemplated by the inventor.

The device of one embodiment of the present invention consists of a pump capable of continuously pumping fluids of arbitrarily high viscosities at a fixed or programmably changing dilution factor, even when the viscosity of the fluid varies immensely (e.g. six orders of magnitude) over time. Such a pump will normally be of the gear, lobe, screw or peristaltic type. This primary pump may optionally use a recirculation of the vessel fluid, to insure fresh sampling at every moment, in which a fraction of this recirculating flow is either continuously, or at intervals, mixed with a larger volume of solvent, which is pumped by a separate pump, for which less stringent specifications are required, since it always pumps a low viscosity fluid. The fluids emanating from the primary and solvent pumps are mixed via a mixing chamber which can take any number of forms; e.g. a microbore 'T' type mixer, an actively stirred micro-chamber, a passive mixer, or combination of the above. Either during or directly after mixing the liquid passes through a vented chamber at atmospheric pressure so that bubbles of gas will be exhaled and not introduced into the detector feed. After mixing, debubbling, and any other conditioning stages (e.g. heating to evaporate monomer), the mixed liquid is pumped by a final pump through the detector train, whose output optionally incorporates another dilution stage, either at high or low pressure, before pumping to the detector train. The detector train itself contains means of determining the concentration, if necessary, of the polymeric or colloidal solute, such that it is not imperative that the dilution be performed to high accuracy.

Because all the pumps used are potentially controllable by a programmable logic controller, personal computer, palm pilot, or other electronic device containing a microprocessor the ability to control both the dilution factor and various flow rates is straightforward.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 3 is a side view of the preferred embodiment of the apparatus of the present invention being used in a flow mode;

FIG. 4 is a perspective view of the preferred embodiment of the apparatus of the present invention being used in a fill mode;

FIG. 5 is a perspective view of the preferred embodiment of the apparatus of the present invention being used in an insert mode; and FIG. 6 is a perspective view of an alternative embodiment of the apparatus of the present invention;

FIG. 7 is a schematic of how a diode laser might be incorporated into a base plate in a ring member version of the present invention;

FIG. 8 is a schematic representation of a 'pinhole mode' of detection;

FIG. 9 is a schematic representation of an 'acceptance angle mode' of detection;

DETAILED DESCRIPTION OF THE INVENTION

Figure 1:
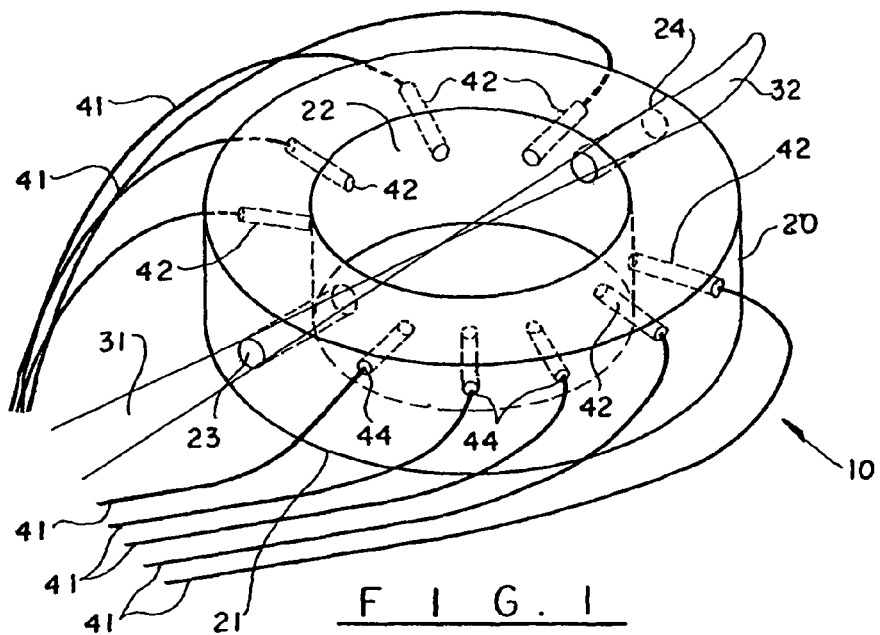
FIG. 1 is a perspective view of the preferred embodiment of the apparatus of the present invention.

The preferred embodiment of the present invention is a submersible light probe 20 (see FIG. 1) including a ring member 21 made of a preferably dark, opaque material, having embedded therein a plurality of optical fibers 41 which can be connected to optical detectors 118 (see FIG. 7) remote from the probe 20. The ends 44 of the optical fibers 41 are preferably in direct contact with the fluid 51 (see FIG. 2) being tested. In a first variation of the invention (see FIG. 3), fluid is caused to flow through the probe 20. In a second variation (see FIG. 4), a base plate 81 is added so that the ring member 21 can contain a fluid to be tested. In a third variation of testing (see FIG. 5), a clear container containing fluid to be tested is placed through the ring member 21. In yet another variation of the invention (preferably only when the probe is not submersible), photodetectors can replace the optical fibers.

The purpose of the probe is to measure light scattering by particles in a fluid (static light scattering (SLS)).

It is believed that this is the first probe for SLS or TDSLS where light detectors (the optical fibers) are actually in the fluid, as opposed to being separated from the fluid by glass or some other media.

FIG. 1 is a perspective view of the minimal ring member version 20 of the present invention. FIG. 1 shows the essential layout of the ring member-version optical assembly 20, with fiber optic detectors 41, beam dump 32, and a laser beam 31 entering a chamber 22 through a window 23, either through local mounting and lensing, or via fiber optic transfer through one of the harness fibers. The ring member channel 22 may alternatively have a square or polygonal cross-section, instead of circular, which may be particularly useful for single or few angle detection. Such single or few angle detection may warrant simply mounting photodiodes on the side of the chamber, rather than using fiber optics. The ring member o.d. and i.d. can vary widely, depending on the application (specific dimensions for test versions are given in the "Experimental Verifications of the Invention", below). The range of i.d. can be, for example, from about 2 mm to 50 cm, with the o.d. being determined by desired wall thickness, which can, for example, range from about 1 mm to 10 cm. The length of the ring member can also, for example, vary from about 3 mm to 10 cm. Optionally a cowl 114 (see FIG. 7) made of rigid or flexible dark material can be placed over the ring member in any of its modes of operation to shield against ambient light.

Figure 2:
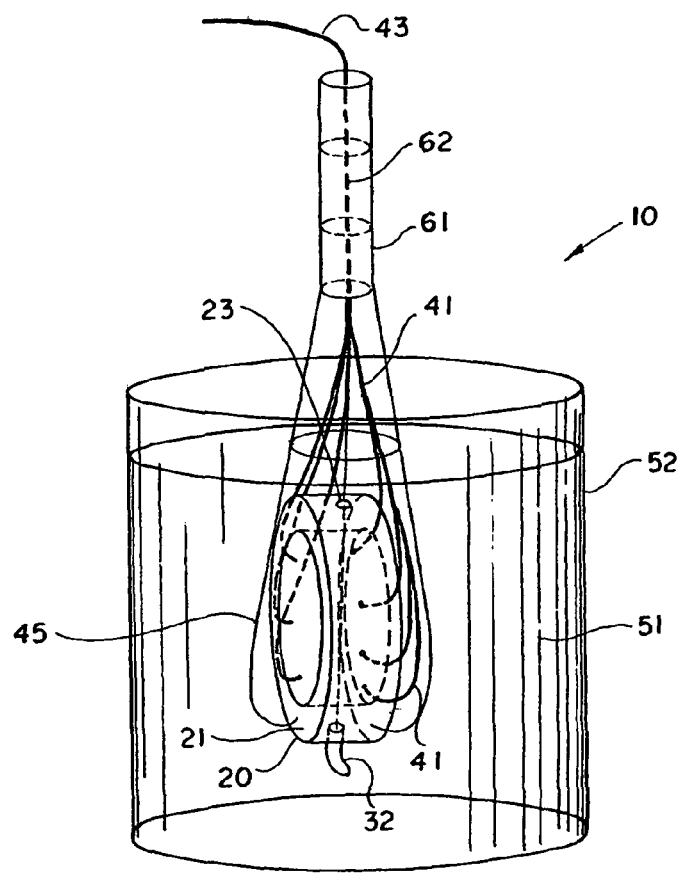
FIG. 2 is a side view of the preferred embodiment of the apparatus of the present invention immersed in a sample liquid.

FIG. 2 shows the immersion mode of the present invention. The ring member assembly 20 is attached to a handle 61. The hollow handle 61 contains an optical harness 43, which has been formed by drawing all the optical fibers 41 together. A sheath 45 on the outside of the ring assembly 20 protects the fibers 41 that are led into the harness 43. A diode laser 62 can be mounted directly on or to the handle 61 for an integral optical assembly/light source version, or the beam can be led in through a fiber optic in the harness 43.

FIG. 3 shows the flow mode of the present invention. Ring member assembly 20 is sandwiched between two end-pieces 71, each of which has a hydrodynamically shaped flow channel 72, and standard HPLC tubing and fittings 73 for liquid to be injected through the ring member assembly 20 via syringe, pump, etc. There are preferably O-rings 74 between the ring member 20 and the end-pieces 71, and the three pieces are held together by through-bolts 75, or a bracket.

FIG. 4 shows the fill mode of the present invention. Ring member assembly 20 can have a base plate 81 attached, so that sample solutions can be pipetted, scooped, or otherwise introduced into the channel, as with dropper 85. A simple modification of ring member assembly 20 could involve not boring the channel 22 all the way through the ring member assembly 20 instead of using a removable base plate 81.

FIG. 5 shows the insert mode of the present invention. A cylindrical vial or cell 92 containing sample solution 91 is simply inserted into ring member assembly 20. This can be advantageous where the sample 91 may be damaging to the ring member assembly 20, or where multiple samples are prepared and stored in vials and are to be measured individually on multiple occasions.

FIG. 6 shows the integral chamber version 100 of the probe of the present invention. By lengthening the ring member version, a one piece unit 100 can serve for both the flow chamber, to which HPLC connections are directly made, and for fill and immersion modes. Chamber o.d. and i.d. follow the ranges mentioned above, whereas the length for any given chamber can considerably exceed the ring member lengths; e.g., lengths can be from about 1 cm to 30 cm. Channel bore 102 can optionally be tapered. In FIG. 6, the laser input 31 can either be through lensing or via fiber.

FIG. 7 is a schematic of how a diode laser 62 might be incorporated on or into a base plate 161 in the ring member version 20 (applicable also to the chamber version 100). Also shown is an optional cowl or hood 114 to cover the ring member assembly 20 to reduce any effects of ambient light. Also shown is the overall schematic of the optical assembly attached via optical harness 43 to the photodiode/electronic assembly 111, which then transmits scattering signals to a microcomputer 112. If a remote laser is used, instead of on the base plate 161, then the laser would normally be housed with the photodetectors 118, and the beam led into the ring member assembly 20 or chamber 100 via a fiber in the optical harness 43. In FIG. 7, a converging lens 63 is used to focus the laser beam.

FIGS. 8 and 9 are schematic representation of detection modes. The 'pinhole mode' (FIG. 8) occurs when the fiber 41 is not completely inserted into the through-hole 42 in the chamber wall, and the angle defined by the end 44 of the fiber 41 and the end of the hole is less than the acceptance angle of the fiber 41 in the particular solvent in which it is immersed. The "acceptance angle mode" (FIG. 9) is when said angle is larger than the acceptance angle of the fiber, which means the acceptance angle of the fiber itself will define the scattering volume 121.

Figure 10:
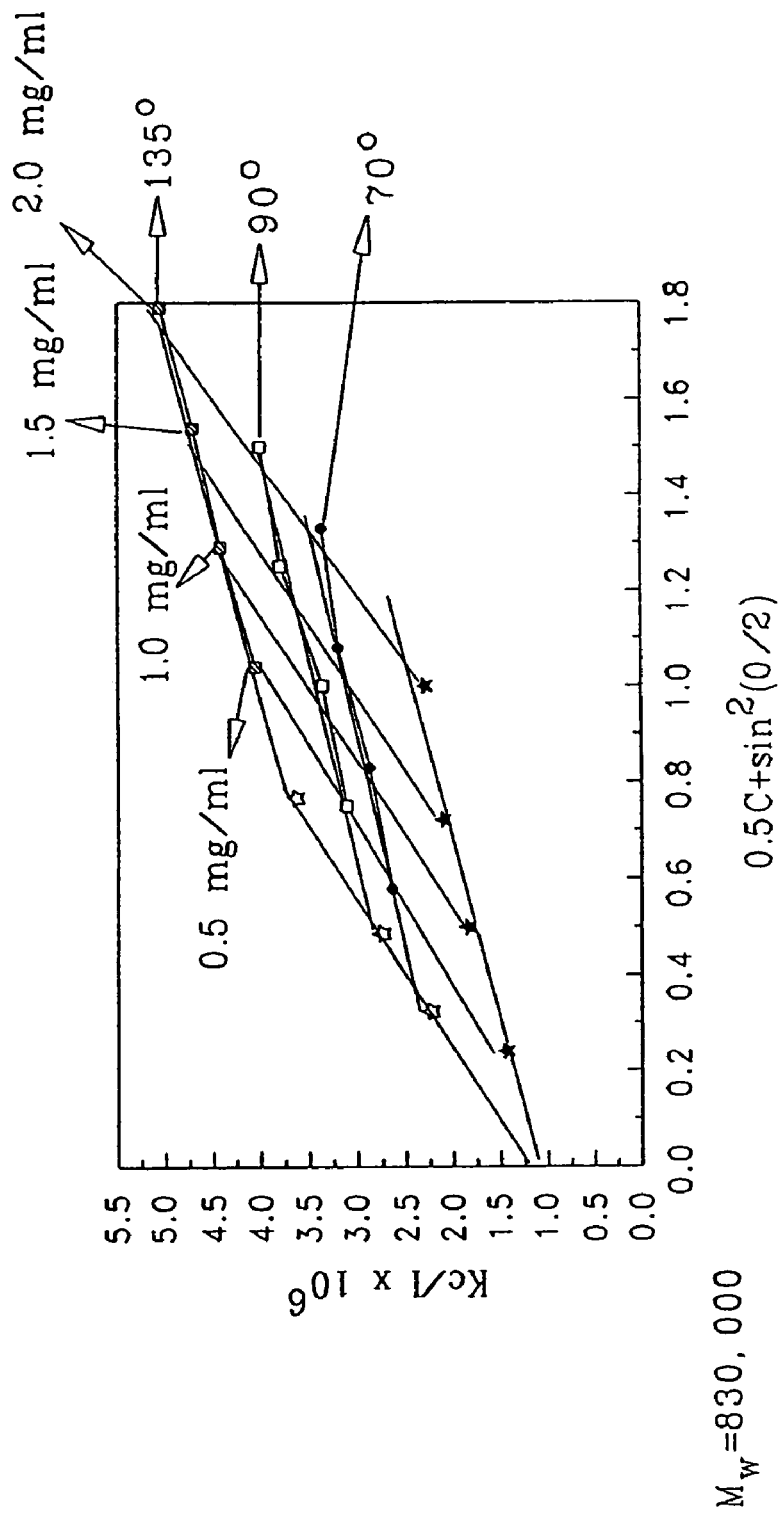
FIG. 10 shows a fill mode Zimm plot for high molecular weight PVP irradiated with a 10 mW Argon ion laser and each angle calibrated to pure toluene.

FIG. 10 shows a fill mode Zimm plot for high molecular weight PVP.

Figure 11:
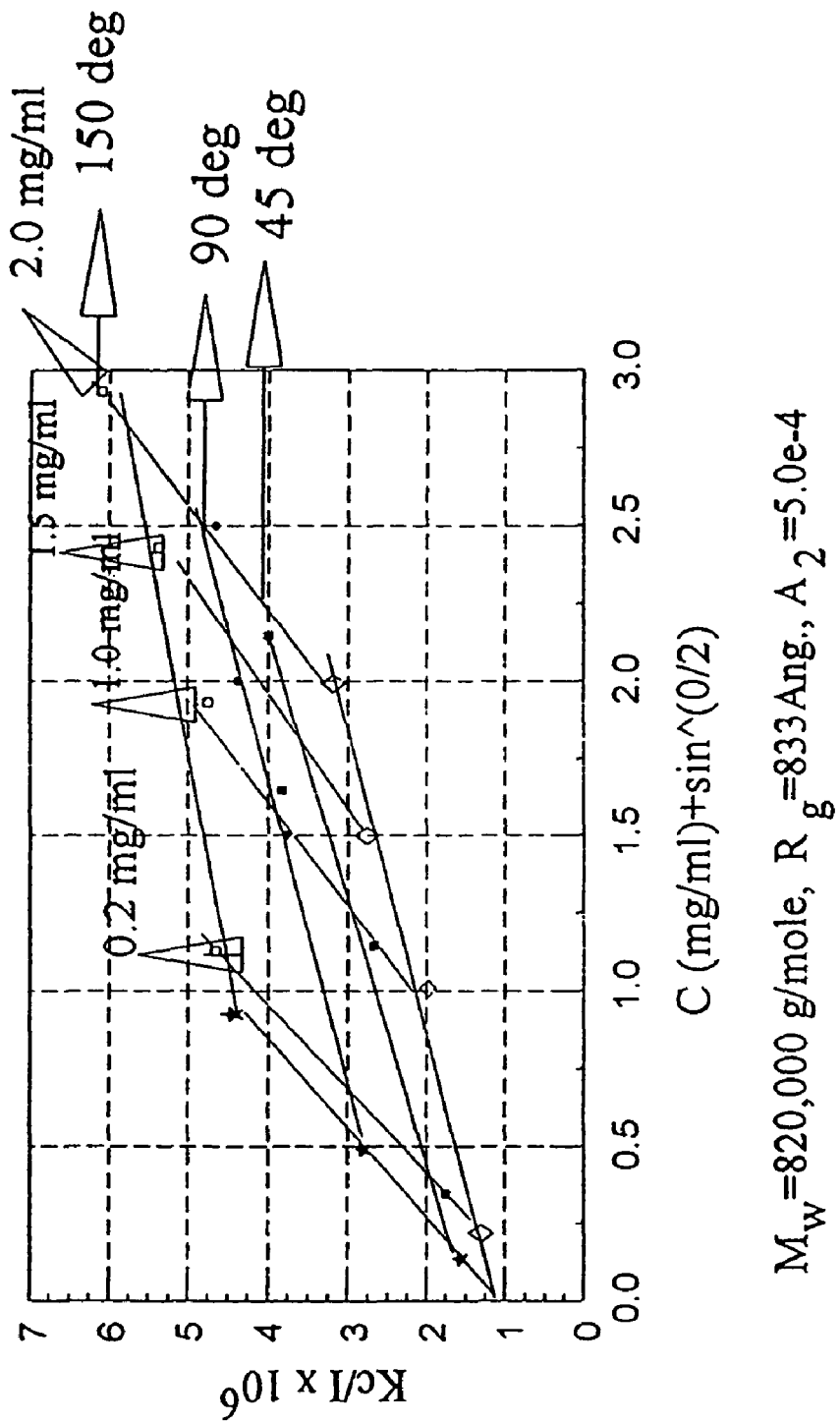
FIG. 11 shows an immersion mode Zimm plot for unfiltered solutions of high molecular weight PVP ("1.3MD" PVP) irradiated with a 10 mW Argon ion laser, using 150 micron optic fiber in 3 inch diameter vessels of solution.

FIG. 11 shows an immersion mode Zimm plot for high molecular weight PVP.

Figure 12:
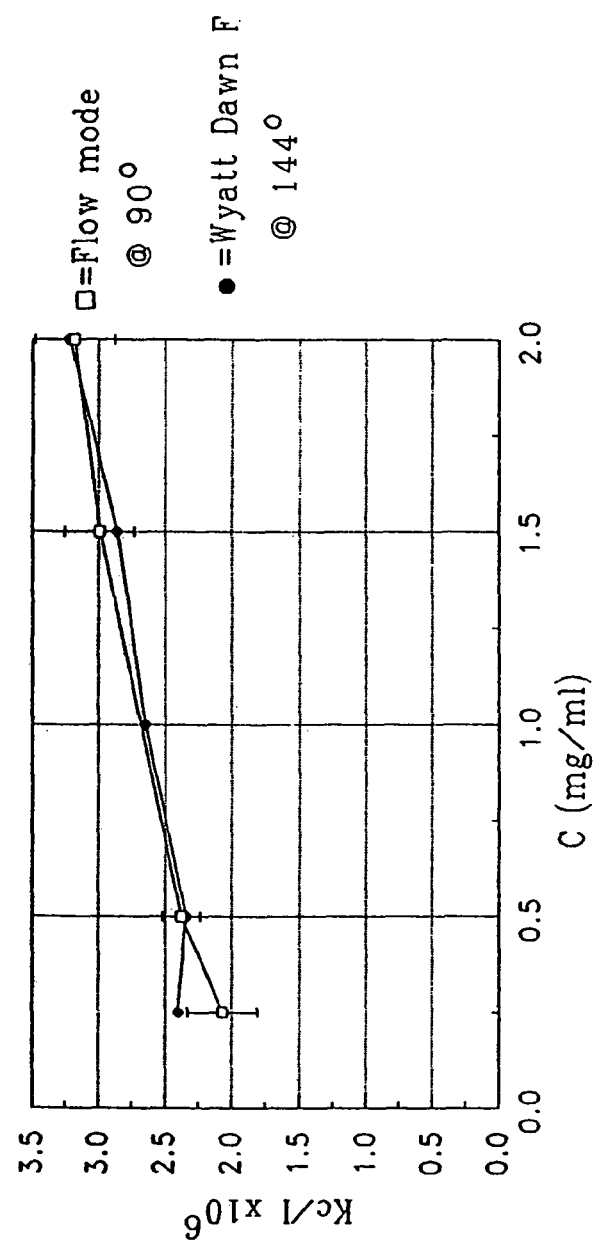
FIG. 12 shows a flow mode Debye plot for high molecular weight PVP at $\theta=90°$ irradiated with a 488 nm Argon ion laser, compared to the results of a Wyatt Dawn-F at 144° (633 nm He—Ne laser), with error bars.

FIG. 12 shows a flow mode Debye plot for PVP at $\theta=90°$.

Figure 13:
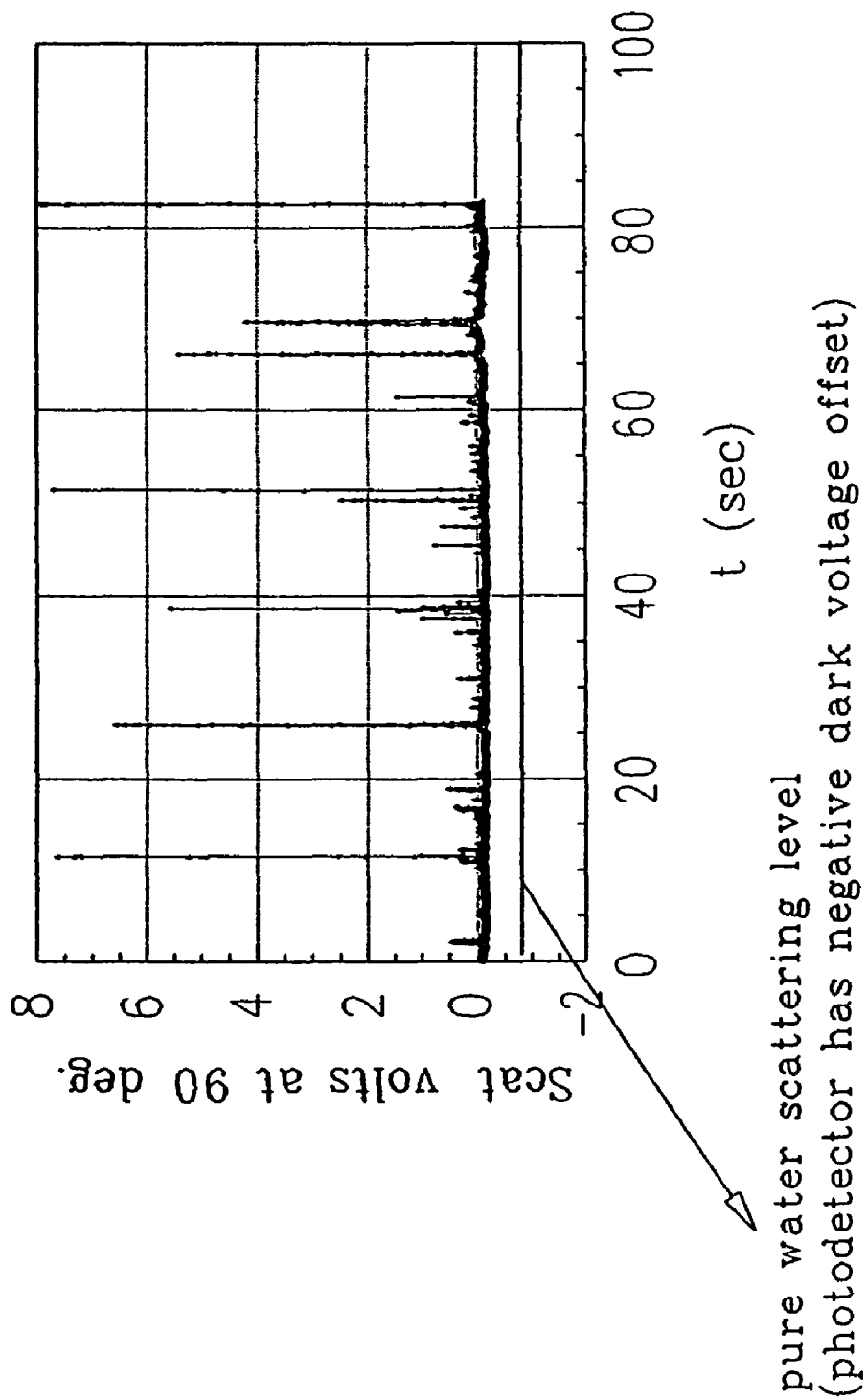
FIG. 13 shows a flow mode measurement of a 0.5 mg/ml high molecular weight PVP (1.3MD PVP) solution with "contamination" by 10 micron latex spheres, using a 300 micron optic fiber at 90° and a 5 mW diode laser.

FIG. 13 shows a flow mode measurement of a 0.5 mg/ml high molecular weight PVP solution with 'contamination' by 10 micron latex spheres. The spheres were in a concentration of 40,000 particles/cc. It is possible both to count the number of spheres passing through the scattering volume, and obtain the absolute scattering due to the PVP, when using the program REEDFLO (see Appendix A of parent patent application Ser. No. 08/969,386 [now U.S. Pat. No. 6,052,184]) on DT2801a. Thus, the present invention can simultaneously conduct absolute macromolecular characterization of one substance and individual particle counting and characterizing techniques on another substance in the same fluid.

Figure 14:
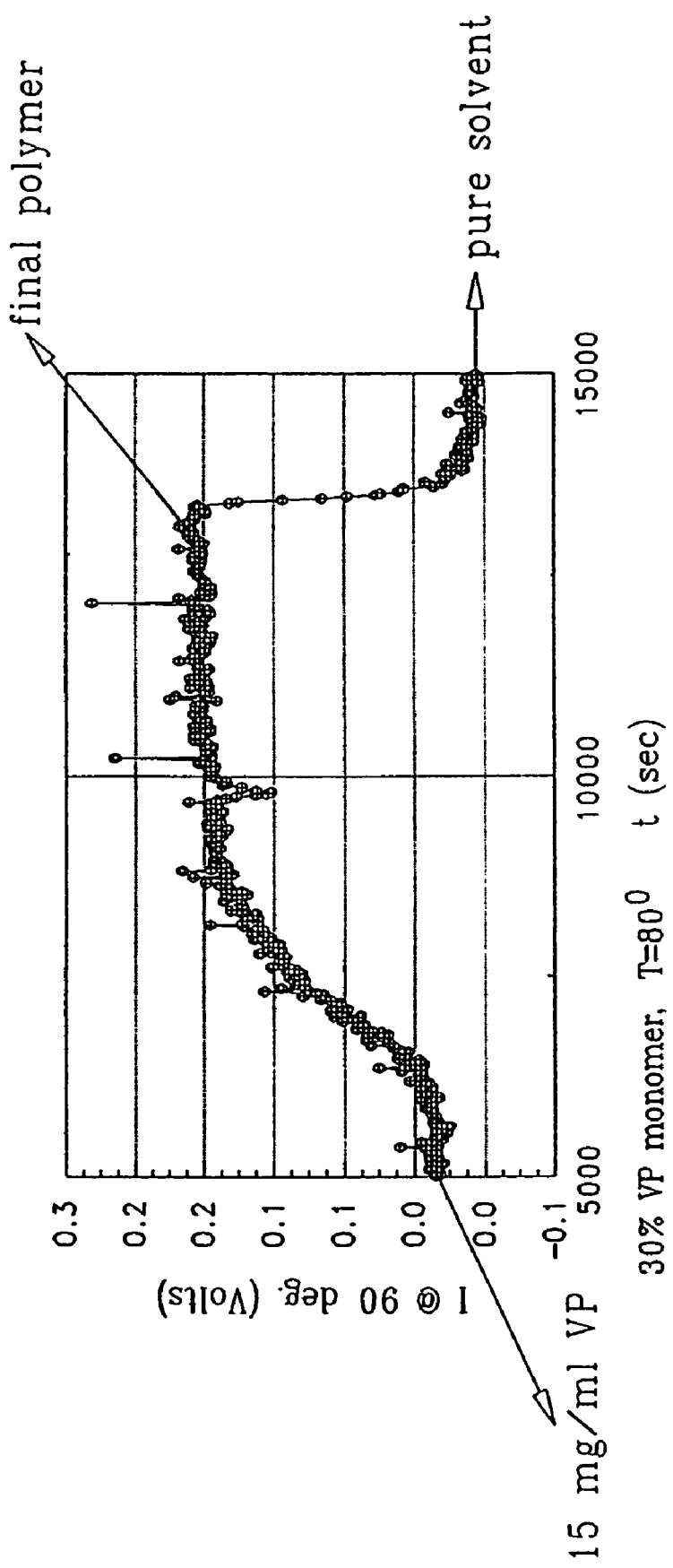
FIG. 14 shows a flow mode measurement of a polymerization reaction.

FIG. 14 shows a flow mode measurement of a polymerization reaction. Vinyl pyrrolidone monomer at 300 mg/ml at T=80° C. is polymerized using hydrogen peroxide initiator. The polymerizing mixture is withdrawn by a mixing pump, which dilutes the PVP to about 6 mg/ml. The diluted mixture is then pumped through the flow cell where the scattering is monitored continuously. Optionally, a concentration detector, such as an index of refraction detector, or ultraviolet or visible spectrophotometer, can be placed in the line of sample flow.

Figure 15:
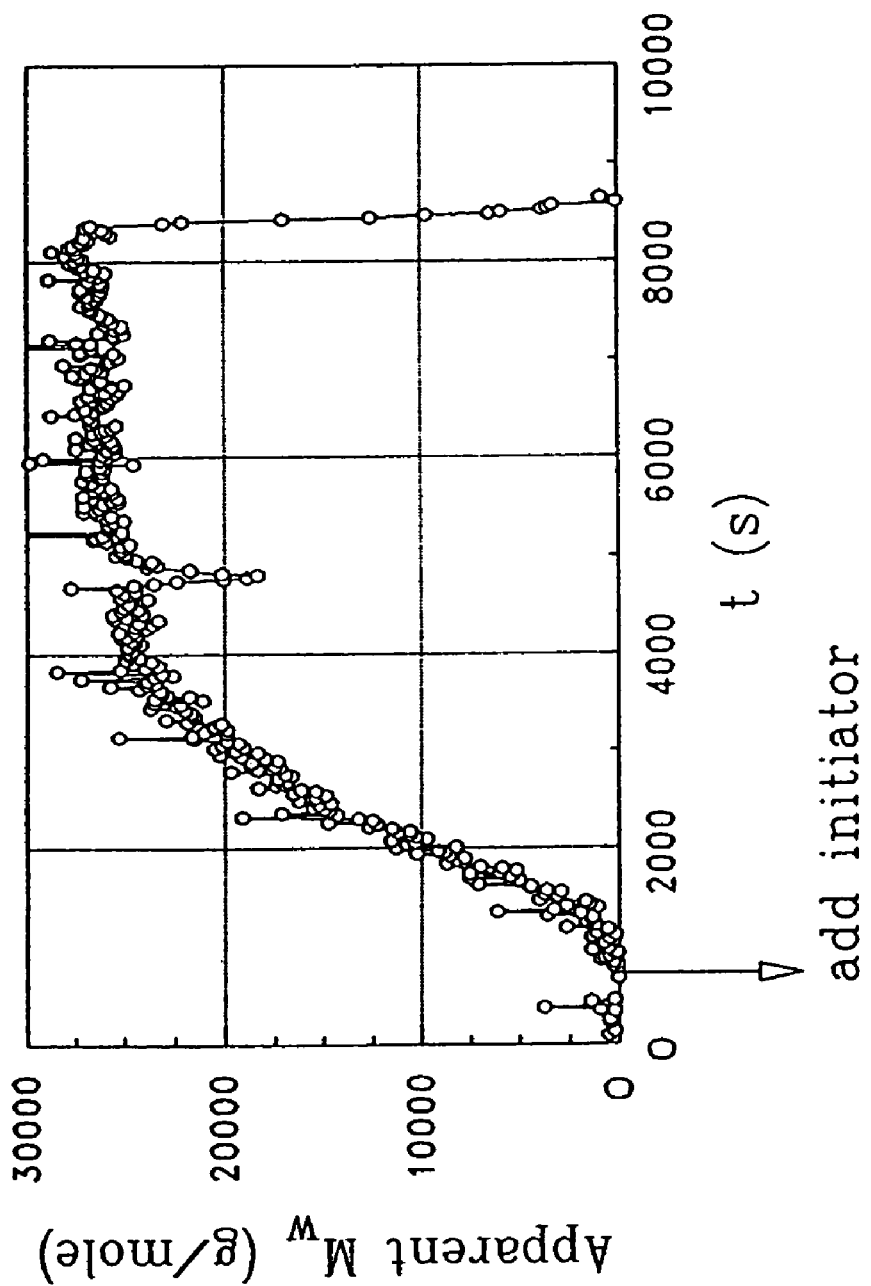
FIG. 15 shows the relative intensity converted to apparent mass (Kc/I) using equations (1)-(3), plotting approximate apparent mass versus real-time for PVP polymerization using a flow mode, using a 300 micron optic fiber at 90° and a 5 mW diode laser, and starting with 300 mg/ml VP diluted to about 6 mg/ml on-line.

FIG. 15 shows the relative intensity converted to apparent mass (Kc/I) using equations (1)-(3).

The preferred embodiment of the present invention consists of an optical assembly 20, from which a harness 43 of fiber optic cables 41 leads out detected scattered light to a remote photodetector and signal processing unit 111, 112, and optionally brings in incident light. The signal processing unit 111, 112 is itself composed of standard components such as photodiodes 118, photomultiplier tubes, amplifiers, discriminators, microcomputer 112, etc.

The optical assembly 20 preferably consists of a solid material. The minimal version consists of a ring member 21 around which the fiber optic detectors 41, incident beam input optics 31, and beam dump 32 are arrayed (see FIG. 1 for this embodiment). The optical fibers 41 are either cemented into holes 42 in the ring member 21, or are affixed with tiny optical fiber chucks (not shown), and are gathered into a ruggedized harness 43, which is led to the photodetector assembly 111, 112. The optical assembly 20 can be connected to a handle 61, which may contain a laser 62, and can be immersed directly in a sample solution 91 (see FIG. 2). The ring member 21 can also be mounted on a base plate 161. The ring member 21 can also serve as a center portion for a segmented chamber, to the endpieces 71 of which are connected hydraulic fittings 73 for fluid to be pumped in and out through in the flow mode (FIG. 3). A small baseplate 81 can be attached to the ring member assembly 20 for fill mode use (FIG. 4), or the bore 22 in the ring member assembly 20 simply need not be perforated all the way through. For insert mode, a sample vial 92 can be inserted directly into the ring member assembly 20 (FIG. 5). In cases where ambient light might give detectable interference, the ring 20 can be covered with a simple cowl or hood 114 in both immersion, fill and insert modes. In the tests presented below, ambient light was not a problem, and no cowl or covering was used.

An integral chamber version 100 (see FIG. 6) can also be made, and consists of a hollow channel or wall 101, normally cylindrical, but which may also have elliptical, square or polygonal cross section. The chief difference between the minimal ring version 20 and integral chamber version 100 is that the chamber 102 is simply longer than the ring chamber 22, so that hydraulic fittings 73 can be directly connected. Furthermore, the extra length provides additional shielding from ambient light, and no cowl or other covering should generally be needed.

In either the ring version 20 or chamber version 100, the internal diameter can be made over a wide range, depending on the application. Typically this diameter will run from about 1 mm to 20 cm. The total channel volume may range, for example, from about 3 to 50,000 microliters, with a preferred range of 10 to 1000 microliters. The wider the channel diameter the less problem there will be with stray light, but more sample solution will be required. In industrial settings, for example, where large volumes of sample are produced, and/or the samples are viscous, high volume cells may be a convenient solution, and pose the most robust and reliable means of achieving low stray light and highest ease of alignment. In situations where sample volume is scarce, e.g. in biotechnology research where only milligrams or less of substance is available, the channel will be made much narrower. Because the optical detection fibers 41 can plug into the same remote array 111 of photodetectors 118, the only change in fabrication in meeting the demands of the high sample volume vs. the low volume user is in the low cost optical probe assembly 20, 100. All photodetection, electronics, computer interfacing and basic software 111, 112 can remain the same.

In the walls of either the ring member or chamber versions, are seated an optical window 23, lens, fiber, or other component for delivering the incident beam into the channel, as well as optical fibers 41 for detection of scattered light placed at any number of scattering angles, usually from about 10° in the forward direction to about 170° in the backscattering direction. A detection fiber can also be placed at the site of the beam dump (0°). The fibers 41 can be cemented into holes 42 in the chamber 22, 102, or held in with tiny optical fiber chucks. Hence, the delivery element for the incident light and the optical fibers are in direct contact with the sample solution, or may be coated with a suitable transparent material, including glass, for protection against deleterious sample solutions. In the case for example where only a single or few angles are desired, small photodetectors (such as photodiodes) can be affixed directly to the outside wall of the chamber, thus eliminating the optical fibers 41.

The body of the optical assembly in either ring member or chamber versions can be constructed of any material suitable to withstand the nature of the sample solution, such as stainless steel, black anodized aluminum, ceramic, Teflon, nylon, polycarbonate, or other plastics. The material is preferably opaque, preferably black or blackened, to minimize glare and stray light.

The power of the incident light is arbitrary, but will typically range from 0.1 to 100 mW. For good detectability and economy, the power range will preferably be from 0.25 to 50 mW. The wavelength can likewise fall anywhere in the visible or ultraviolet range. Since there are no requirements for coherence (unless a single mode optical fiber is installed optionally to collect light for dynamic light scattering, in which case a laser light source would be required), nor does the incident light have to be extremely monochromatic (a bandwidth of 50 nm would not be excessive), the light source does not have to be a laser. As such, conventional white light, broad band, or discrete line sources, such as arc lamps, light emitting diodes, vapor lamps and incandescent sources are all possible candidates for the incident light. By the same token, if a multiple wavelength source is used, it is possible to vary the scattering vector q ($q=4\pi n/\lambda \, sin(\theta/2)$) by introducing different discrete wavelengths and detecting at a single angle; e.g. by selecting wavelengths with a monochromator in front of a white light source and introducing these into the input optics. Using light from around 200 to 800 nm could yield a factor of four variation in q. This could avoid use of multiangle detection, and require only a single fiber optic for detection and single photodetector/amplifier. On the other hand, if both multi-angle detection and multiple wavelengths are used then, say, for wavelengths from 200 to 800 nm, and scattering angles from 15° to 170°, the factor of q can be varied by as much as a factor of 30. Appropriate collimation and/or focusing optics are usually needed to introduce the source beam into the channel.

In many applications use of a laser may be preferred. A laser source would preferably be around 200-1000 nm, and more preferably 450 to 780 nm, where the majority of economical, low power, commercial lasers operate. The laser beam is preferably focused at or near the center of the hollow channel, although an uncollimated, or reduced and re-collimated beam will also work. The beam waist can range from the diffraction limit of Gaussian beams ($\lambda f/D$, where $\lambda$ is the incident wavelength, D the unfocused laser beam waist diameter and $\lambda$ the lens focal length) typically on the order of 1 to 200 microns, up to a 2 mm unfocused beam. The preferred beam waist diameter will depend on the intended application, and would be given as an option to a potential user of the invention, according to their needs. For example, measurement of dilute solutions of small, clean solutions would tend to use a wider beam waist, whereas concentrated solutions containing significant stray scatterers would preferably use a very highly collimated beam. Use of a highly focused beam and detectors defining a small scattering volume allows less probability of finding large particles in the scattering volume at any instant. When a large particle enters, either with the sample stationary or under flow, a large spike is produced which can then be recognized and discriminated against, in order to recover the absolute scattering from the desired scatterers. Sufficiently fast detector response allows spikes to be identified, counted (for purposes of large particle counting), and eliminated, to recover the desired background scattering.

The method of delivering the beam can be directly through an optical window on the chamber, via a tubular transfer lens, such as the endo-index type, or via an optical fiber, either flexible or rigid, with such lenses, pinholes and other light handling components as is necessary to deliver the beam in focused or collimated fashion, with the desired beam waist, and with a minimum of glare and stray light. If the beam is delivered by optical fiber, the laser can be remote from the optical assembly. Alternatively, the laser can be mounted directly to the optical assembly (FIG. 7).

Directly across from the incident beam is a beam dump 32 for the incident beam 31 to minimize 'glare' and stray light. This beam dump 32 may be of any standard type, ranging from a hole, to a 'Rayleigh horn', to a complete sub-system involving coated or un-coated lenses, and/or prisms, mirrors, a photodetector, or other optical components.

The optical fibers 41 may be of the multimode variety, whose inside diameter may range from 10 to 1000 microns, the smaller sizes being preferred where highly scattering samples are being measured, or for subsequent use with dynamic light scattering. In fact, a single, relatively large fiber diameter may be selected, such as 500 microns, and a rotatable, annular mask can be affixed to the channel wall, which would have varying diameter pinholes for defining the field of view of each optical fiber. Alternatively, the cell interior may be permanently outfitted with sets of different diameter fibers, spaced closely about each selected scattering angle, all of which could be continuously monitored. The fibers themselves can be of virtually any commercial or research grade. They must be chosen, however, so as to be compatible with the solvent and sample conditions where the invention will be applied. Where toluene is used, for example, the fibers must withstand that solvent, so glass core fibers with glass cladding and buffer would be preferred, or some similar substitute, such as glass core with CPE (chloropolysulfatal ethylene) jacket from Belden corporation.

The way the optical fibers 41 are attached to the cell 21, 101 helps to define the scattering volume. If the fibers reach through the cell to the surface of the channel (chamber) 22, 102, then the scattering angle will be defined by both the acceptance angle of the fiber in the particular solvent the cell contains, and the beam waist. Definition of the scattering volume in this way can be termed the 'fiber acceptance angle mode'. If the fiber 41 is recessed back into a hole 42 in the chamber to the point where the angle subtended by the two ends of the cylindrical hole 42 is less than the acceptance angle of the fiber 41, then detection can be said to be in the 'pinhole mode'. The difference in detection modes is shown schematically in FIGS. 8 and 9.

The optical harness 43 leads all the detection fibers to a remote bank 111 of photodetectors 118. The fibers 41 can be coupled to their respective detectors 118 by inserting them into permanently aligned quick connect optical fiber connectors, as are commercially available (e.g. Newark Corp. or Amphenol Corp.), positioned in front of the detector surfaces.

The optical assembly can be used in several modes. In one of its submersible modes, the assembly 20, with no additional modifications, can be directly submerged into a sample solution 91 contained in a test tube 92, industrial tank, etc. As a remote, fill mode unit, the channel may be capped at one end (or the channel simply does not have to be bored completely through), which allows a small quantity of sample to be pipetted, scooped, or otherwise introduced into it and reside in it, remotely from the main sample supply, if desired. Each end of the channel may also be outfitted with a coupling to accept a fluid flow, so that the assembly may also be used in flow mode, such as for monitoring, optionally with on-line dilution, unfractionated polymers degraded or produced in a vat, fractionated polymers from Size Exclusion Chromatography, capillary hydrodynamic fractionation, etc. In this mode of operation it may be desirable to hydrodynamically taper the interior to optimize the flow past the plane of the optical fibers and incident beam. The invention can also be used in insert mode, whereby samples in sealed cells or vials can simply be inserted into the ring member or chamber, in the traditional fashion. In this case, one returns to the common situation in which there is a transparent cell between the sample, incident beam and detection optics.

The invention can be simultaneously cleaned and absolutely calibrated by use of an appropriate solvent such as toluene, whose absolute Rayleigh scattering ratio is known. The probe is immersed in the solvent, or the solvent made to flow through it for cleaning purposes. At the same time, the solvent scattering is monitored, and when it reaches a steady value, this is used for determination of the absolute calibration factors for each detection fiber.

As regards the minimal ring member version, it can be used submersibly on its own or become a central portion of a three piece unit. This may be desirable for purposes where quick interchange of optical assemblies to different specifications, cleaner or newer units are made, etc.

In both the ring member version 20 and integral chamber version 100, an outer protective sheathing 45, such as a ring member of plastic or metal may slip over the fiber optics 41 protruding externally from the ring member 21 or chamber wall 101. Likewise, in all cases, the entire optical assembly, whether a ring member or chamber, can be placed within a completely enclosed housing, into which sample can be introduced either by flow or immersion. Such a housing may be desirable when the optical assembly needs special protection from a harsh (e.g. high temperature) environment, or is immersed in turbulent or otherwise potentially damaging or signal distorting liquids.

The present invention includes the aforementioned ring member or integral chamber SLS probe. The incident beam 31 is introduced into the device via optical window 23, or a fiber optic and/or tubular lens and other optical elements, and scattered light is taken out via fiber optics 41 whose tips 44 are arrayed at various angles in the horizontal plane of the ring member 21 or chamber wall 101. All the optical fibers 41 and elements are drawn together into an 'optical harness' 43, which is led to the 'outside world' through a hollow handle 61 on the device 20. The optical fibers 41 carrying scattered light and issuing from the harness 43 are coupled to conventional optical detectors 118 (e.g. PIN or avalanche photodiodes, photomultiplier tubes, etc.), whose voltage or current signals are led to a conventional signal processing device and/or into a computer 112. The optical probe portion consists essentially of a piece of material, preferably dark, with optical fibers and a few other inexpensive optical elements (such as borosilicate windows 23) attached into a harness. As such, the probe itself should be quite inexpensive and could even be disposable. The photodetectors 118, signal processing and computer analysis portions of the instrument are remote and permanent (although quite portable), and represent the major cost. In some cases, especially where few angles are involved, and submersible operation is not a priority, photodetectors (e.g. photodiodes) can be mounted directly to the chamber, thus avoiding use of the fiber optic detectors.

In the submersible mode, calibration (and cleaning) can be done by merely immersing the probe in a calibration solvent, kept handy in a closed vessel. This could be toluene, or any other solution whose absolute Rayleigh scattering ratio is known.

The software in Appendix A of parent patent application Ser. No. 08/969,386 (now U.S. Pat. No. 6,052,184) can serve as a basis for data reduction, analysis and display. Data can be collected and reduced either on a standard microcomputer, or by building a customized microprocessor based unit. The software can include programmed criteria for averaging scattering signals, identifying, counting and rejecting scattering spikes from large, stray scatterers, and informing the operator when signal collection is done. Software can access on-board libraries to inform the operator of likely phenomena occurring in the sample (e.g. aggregation, gelation, degradation), and problems such as poor solution quality (e.g. too much 'dust'), presence of aggregates, or other anomalies.

Experimental Verifications of the Invention
I) Fill Mode Tests:
A) Transfer Lens Version/Single Angle A first prototype of the invention in the integral chamber version was made in order to assess whether absolute macromolecular characterization, in terms of molecular mass, was feasible. This is meant to be only a demonstration of the feasibility of the invention, not a highly precise absolute molecular mass determination nor critical comparison of the invention's performance with a commercial instrument.

Dextran of nominal mass 200,000-300,000 g/mole was selected for the measurement. It was mixed at 0.003 g/cm$^3$ in an aqueous solvent containing 0.1 Molar $NH_4NO_3$ and 0.1% sodium azide for protection against bacterial contamination. There is nothing special about this particular solvent, and even pure water would have been adequate (since dextran is a neutral polymer and is not subject to the unusual physical effects that charged polymers display in pure water).

An optical unit was fabricated from a 1⅞" inch long piece of, e.g., black nylon round stock of ⅝" o.d. An inner, cylindrical channel of diameter 7.7 mm was bored concentric with the axis. The inner ends of the channel were tapped to accommodate standard ⅜" plugs, barbs and other hydraulic fittings. Perpendicular to the cylinder axis, a hole was drilled to accommodate a 1.98 mm o.d. Endogrins® lens, obtained from Edmund Scientific Co. Straight across from this hole on the opposite side of the channel a larger diameter hole was drilled for use as a beam dump. At 90° to the incident light hole a small hole was drilled to accommodate an optical fiber with inner core 100 microns and cladding 140 micron o.d. The fiber was inserted into the hole in the channel, and was found to work best when protruding but slightly from the hole into the channel. Both the fiber and lens were secured in their holes with optical putty. The opposite end of the fiber, which was about two feet long, was secured remotely from the optical assembly into a fiber optic chuck from New Focus Co., and butted up against the photosensitive surface of a Hammamatsu photodiode with integral FET op-amp, contained inside a light-tight box, containing both the diode/FET and an additional standard operational amplifier stage.

The amplified signal was fed into a Nicolet 4094B digitizing oscilloscope, although any data collection device with a rate of 1 KHz or faster would have sufficed. Sampling at 1 KHz or faster allows spikes from diffusing impurity particles and fluctuating scattering levels to be recognized and rejected, leaving the desired signal from the polymer or colloid scatterers. In fact, spike and fluctuation rejection was used in this and other tests.

Light of wavelength 488 nm and approximately 20 mW was from a Coherent Corp. Argon ion laser, which had an output beam waist of about 2 mm. The light could be delivered either highly focused or uncollimated. For high focusing, a 5 mm lens with a focal length, f=5 mm from Edmund Scientific was placed external to the optical assembly, and led to a beam waist of about 1.5 microns. This was transferred into the channel of the optical assembly via the 1.98 mm Endogrins® lens, which was 6 cm long. Alignment of the delivered beam with respect to the detection fiber optic at 90°, and signal maximization for this arrangement was achieved by using a solution consisting of a ¹⁄₄₀ dilution of 190 Angstrom latex spheres from Duke Scientific, although any moderately scattering solution, such as water with a tiny drop of milk or coffee creamer powder, would be adequate.

The system was then tested by measuring, sequentially, the photodiode dark count (i.e. with no laser beam entering the optical assembly), the photovoltage with pure water, with a 3 mg/ml solution of dextran, and toluene. The various liquids were introduced into and removed from the cell with a long, glass pipette with a rubber suction bulb at one end. The photovoltages are listed below:

$$I(q) = \frac{V(q) - V_s(q)}{V_c(q) - V_d(q)} I_c f \quad (3)$$

where $V(q)$ is the photodetector voltage from the sample scattering at wave vector q, $V_s(q)$ is the scattering voltage at q of the pure solvent in which the polymer or colloid is dissolved, $V_c(q)$ is the scattering voltage of the calibration solvent scattering at q, and $V_d(q)$ is the dark voltage of the photodetector at q. $I_c$ is the known, absolute Rayleigh scattering ratio for the calibration solvent. For toluene at 25° C., $I_c$=1.406×10⁻⁵ cm⁻¹ at 633 nm, and 4.96×10⁻⁵ cm⁻¹ at 488 nm. In equation 3, f is an optical correction factor, given approximately as $(n_{sample\ solvent}/n_{calibration\ solvent})^3$. This accounts approximately for the difference in field of view and detector solid angle for optical fibers in the chamber.

For water n=1.333 and for toluene n=1.494 so that f is approximately 0.71.

The results for the dextran are shown in the above table. The apparent mass of 174,000 (at θ=90°) is obtained from the invention and 191,000 from the Wyatt Dawn F (at θ=144°). At these angles, $q^2$ is approximately the same for each instrument. At any rate, $R_g$=225 Angstroms for this Dextran (as measured on the Dawn F), so that there is very little $q^2$ dependence over the visible light range.

Table of Photovoltages (accuracies are to about +/− 1 mV)

| measured | volt. (mV) | scattering difference | K | Rayleigh ratio, I(cm⁻¹) | Kc/I | app. M (θ = 90°) | app. M Wyatt Dawn-F (θ = 144°)** |
|---|---|---|---|---|---|---|---|
| Photodiode dark voltage | −65 | NA | NA | NA | NA | NA | NA |
| pure water | −57 | NA | NA | NA | NA | NA | NA |
| 3 mg/ml dextran | −30 | $I_{dex} - I_{water}$ = 27 | 1.46 × 10⁻⁷ | 7.63 × 10⁻⁵ | 4.23 × 10⁻⁶ | 174,000 | 191,000 |
| toluene | −51 | $I_{tol} - I_{dark}$ = 14 | NA | 3.96 × 10⁻⁵* | NA | NA | NA | dn/dc = 0.142 for dextran
*This is the known Rayleigh ratio for toluene at T = 25° C. for λ = 488 nm.
**This is the proper angle for comparison, since the Dawn-F was used with a 632 nm He-Ne laser, and the test chamber with a 488 nm Argon ion laser.

The Zimm equation for SLS, when $q^2 \langle S^2 \rangle \ll 1$ is $$\frac{Kc}{I} = \frac{1}{M_{app}} = \frac{1}{M_w}\left(1 + \frac{q^2 \langle S^2 \rangle_z}{3}\right) + 2A_2 c \quad (1)$$

where I is the excess Rayleigh scattering ratio from the polymer solution (the total scattering minus the pure solvent background). $M_{app}$ is the apparent mass, defined as per the equation (i.e. it neglects the effects of finite $2A_2c$ and $\langle S^2 \rangle_z$ effects). $M_w$ is the weight averaged polymer mass, $\langle S^2 \rangle_z$ is the z-averaged radius of gyration, $A_2$ is the second virial coefficient, c is the polymer concentration in g/cm³, and K is given, for vertically polarized light, $$K = \frac{4\pi^2 n^2 (dn/dc)^2}{N_A \lambda^4} \quad (2)$$

where n is the index of refraction of the sample solvent (n=1.33 for water), and λ=4.88×10⁻⁵ cm, is the vacuum wavelength of the incident light.

The absolute scattering I was calculated according to

The fact that the apparent mass from the invention is within 10% of the value of that obtained from an established instrument clearly demonstrates the feasibility of making absolute molecular mass determinations. Refinement of the instrumentation should make results even more accurate. At any rate, it is generally recognized in the SLS field that molecular weights of polydisperse samples are seldom accurate to more than a few percent.

B) Multiple Angles

A similar chamber (with no hydraulic fittings) was made except that it was outfitted with detection fibers at 70°, 90° and 135°, and two opposed 3 mm sapphire windows, glued into holes in the chamber, were used for beam ingress and egress. Toluene was used for absolute calibration at each angle. Zimm plot results from a solution of high molecular weight PVP are shown in FIG. 10. Ten mW of argon ion laser power were used, and a 50 mm focal length lens was used to focus the laser beam through the window in the chamber.

II. Immersion Mode Test:

An immersion cell was constructed from nylon roundstock of 16 mm outer diameter and 12 mm i.d. and 8 mm long. 150 micron optical fibers were glued in with epoxy at 45°, 90° and 150°, with their front surfaces at the level of the inner cell diameter face. Two 3 mm holes were cut in opposite ends of the cylinder, and were left empty for the tests (i.e. neither entrance window nor beam dump were used). The optical fibers leading to the remote detector were secured so that no additional bending or deformation of them occurred, since additional bending or deforming leads to large losses in transmitted light. A tubular stainless steel handle was attached to the cylinder to allow for manipulation. The cylinder was immersed in 3" diameter beakers containing the test liquids, and the handle, protruding from the solution, was secured with a ringstand. 20 mW of Argon ion laser power were delivered in a beam from above the beakers, and a 50 mm focal length lens was used to focus the light in the center of the cylindrical chamber.

Scattering tests at the three angles were carried out using 0.2, 1.0, 1.5 and 2.0 mg/ml solutions of a high molecular weight polymer, PVP. A digitizing oscilloscope was again used to monitor the detected light at each angle, one at a time. These solutions were unfiltered. Identification and rejection of spikes from large impurity particles diffusing through the scattering volume and fluctuating signals from other causes allowed this unusual series of measurements on unfiltered solutions to be made. The scattering voltage of toluene at each angle was used to find the absolute calibration factor at each angle. FIG. 11 shows typical results. These compare quite favorably with the results for the fill mode example above (1-B).

III. Flow Mode Tests

A 3-piece flow cell was constructed out of nylon roundstock of 16 mm o.d The central portion was 8 mm long, with a 7 mm bore, and contained a single 300 micron fiber epoxied in at a scattering angle of 90°. Two 3 mm sapphire windows were mounted on opposite sides of the central bore, one for laser beam ingress, the other for egress. Endcaps of the same material and o.d. pressed on each side of the central portion and O-rings created a seal. Round aluminum plates outfitted with long bolts served to clamp the endcaps to the central piece. The endcaps each had a small hole drilled in them for fluid to reach the bore of the central portion, and each was outfitted with a standard GPC fitting, allowing attachment of standard PEEK (polyethyleneethyleneketone) HPLC (high performance liquid chromatography) tubing to allow liquid samples to be pumped in and out.

The basic construction of the center portion can be identical to that of the immersion cell, making the two ultimately interchangeable, or at least slight modular variations of each other. Also, these cells can easily become fill mode cells by simply adding a base plate (as in the drawings).

A) Debye Plot at a Single Angle

Solutions of high molecular weight PVP of concentrations 0.25, 0.5, 1.5 and 2.0 mg/ml were pushed through the cell manually with a syringe, at roughly 1 ml/min. The experiment was repeated several times and error bars obtained. Kc/I at θ=90° is shown in FIG. 12, along with the associated error bars, and a comparison with results from a Wyatt Dawn-F. Ten mW of argon ion laser power were used, and a 50 mm focal length lens was used to focus the laser beam through the window in the chamber.

B) Discrimination Against Large Particles

The present inventor wrote program REEDFLO (see Appendix A of parent patent application Ser. No. 08/969,386 [now U.S. Pat. No. 6,052,184]) to capture data through a DT2801-a analog-to-digital converter board and perform averaging and data storage functions. Maximum speed is about 40 microseconds per point with this board, and up to eight separate detectors can be monitored per board in the differential input mode. The idea was first tested as to whether the flow cell with small scattering volume could usefully measure both absolute polymer scattering levels and identify and count spikes from large particles. Ten mW of argon ion laser power were used, and a 50 mm focal length lens was used to focus the laser beam through the window in the chamber. The scattering volume was roughly $5 \times 10^{-7}$ cc.

To this end a mixture of 0.5 mg/ml PVP of molar mass around 106 grams/mole was mixed with Duke Scientific 10 micron latex spheres such that the sphere concentration was $4 \times 10^4$ particles per cc. This gave roughly an average of 0.02 particles per scattering volume. The solution was pushed through the cell manually using a syringe, roughly at a flow rate of 1 ml/minute. The 5 mW diode laser (wavelength=635 nm) was used as the light source.

FIG. 13 shows that the cell was capable of measuring both the homogeneous background scattering from the polymers, and both identify and count the number of large particles in the flowing sample. Given the pure solvent level shown on the drawing, it is hence possible to recover the absolute intensity scattered by the homogeneous polymer background scattering. A significant degree of contamination by large particles can hence be tolerated in this system.

C) Kinetics of Polymerization

The kinetics of polymerization were carried out in real-time using the flow cell. A 5 mW diode laser was used, and a 50 mm focal length lens was used to focus the laser beam through the window in the cell. A 30% solution of vinyl pyrrolidone (VP) monomer was mixed in water with 0.1% ammonia, and the solution heated to 80° C. The polymerization was initiated with 0.7% hydrogen peroxide. At high concentrations, such as 30% VP, there is very little change in light scattering intensity as polymerization proceeds (i.e. in eq. (1) $2A_2c$ is much larger than $1/M_w(1+q^2<S^2>_z/3)$). Hence the reaction solution must be diluted for TDSLS to be a useful monitor of $M_w$ in real-time. To do this, concentrated reactant is withdrawn with a pump and mixed with solvent from a separate reservoir of pure solvent. This can be achieved by using a hydraulic 'T' one arm of which goes to the concentrated reaction solution, and the other to the pure solvent, with the mixed output being then pumped out by a pump and forced through the scattering flow chamber. It turned out that use of a programmable mixer was more convenient for mixing reactant and pure solvents. A standard ISCO (corporation) 2350 HPLC pump was used to pull mixed material from this pump and push it through the flow cell and refractive index (RI) detector, which was placed in series with the flow to measure the concentration, and any possible variations, of the diluted sample. For this experiment the reaction mixture, initially at 30% VP, was diluted so that the sample passing through the flow chamber was at 6 mg/ml.

FIG. 14 shows the results of a polymerization reaction in terms of scattered intensity in arbitrary units vs. time, whereas FIG. 15 shows the approximate apparent mass, obtained by eqs. (1)-(3). The apparent mass is simply 1/Kc. For PVP of mass about 30 kD, there is no significant angular dependence, so $q^2<S^2>\sim 0$. Furthermore, $A_2 \sim 5 \times 10^{-4}$ so that at a PVP concentration of 0.006 g/cm³, $2A_2cM_w \sim 0.18$. Such a correction to the apparent mass, about 18%, is easily taken into account.

Preferably, optical fibers 41 are attached to ring member 21 with fiber optic light chucks, such as those commercially available from Upchurch Company.

Figure 16:
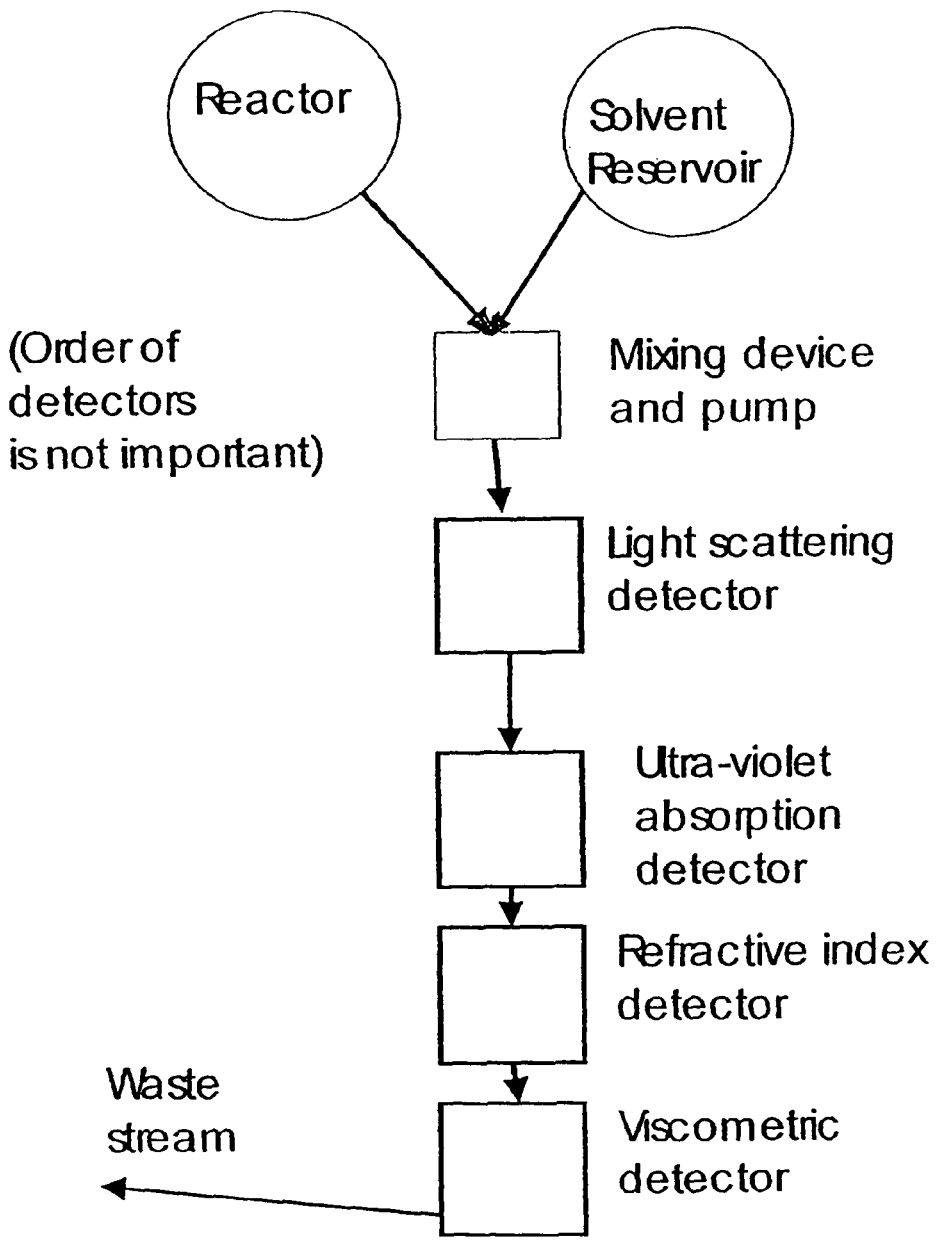
FIG. 16 illustrates the scheme used by the inventor et al. (ref. 6) for the online monitoring of a poly(vinyl pyrrolidone), or PVP, reaction.
Figure 17:
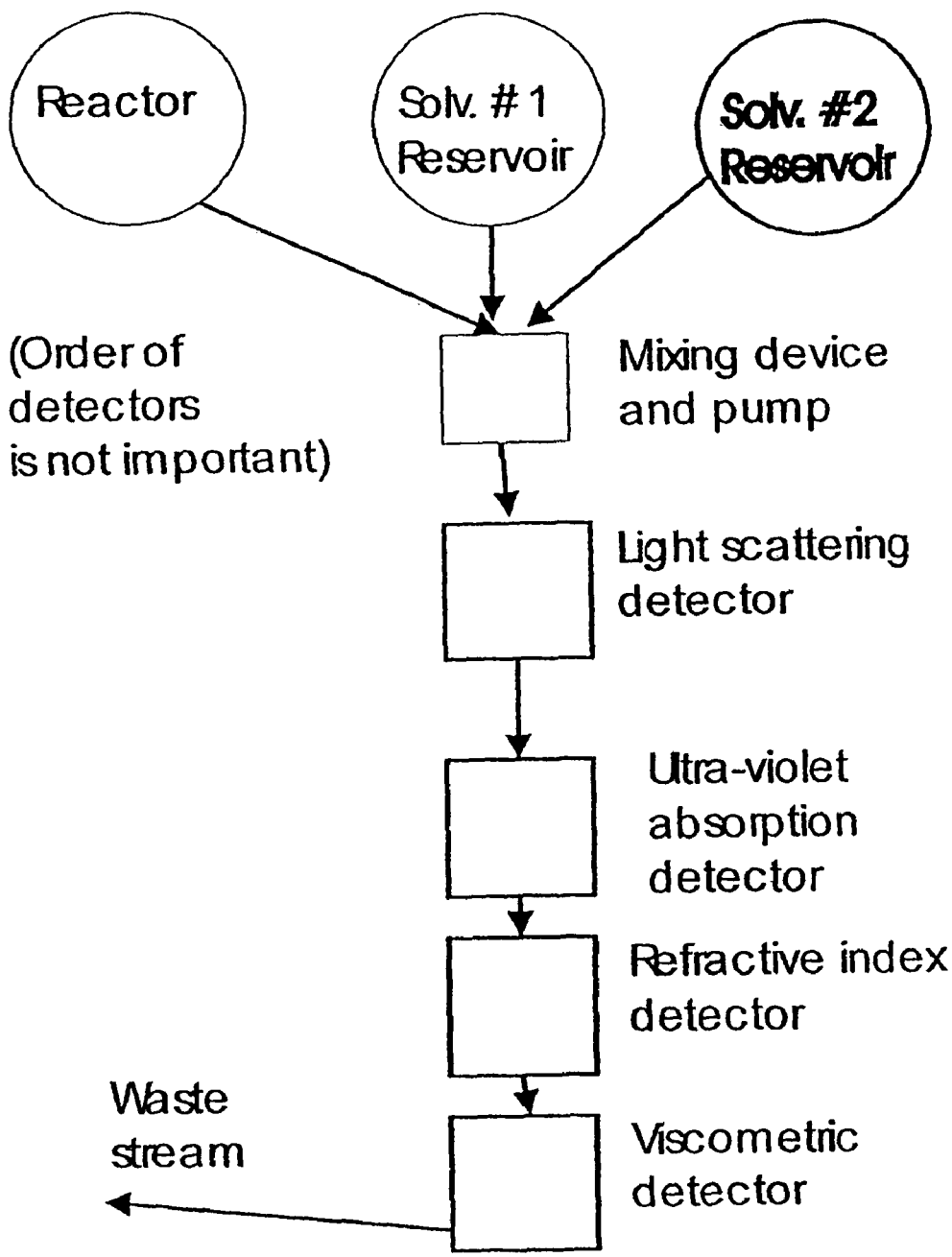
FIG. 17 shows a three vessel scheme, wherein one vessel contains the polymer or colloid to be characterized, and two other vessels are used, each of which contains different solvents.

FIG. 16 shows apparatus for an online measurement of $M_w$, monomer conversion, total solute concentration and reduced viscosity during a polymerization reaction. The method and results are described in detail in Florenzano, Strelitzki and Reed, *Macromolecules*, vol. 31, pp. 7226-7238, 1998, "Absolute, On-line Monitoring of Molar Mass during Polymerization Reactions". In summary, vinyl pyrrolidone monomer at 200-300 mg/ml at T=60-80° C. was polymerized using hydrogen peroxide initiator. The polymerizing mixture is withdrawn by a mixing pump, which dilutes the PVP to about 6 mg/ml. The diluted mixture is then pumped through the light scattering, ultra-violet absorption, viscosity and refractive index detectors, whence the mentioned polymer properties are obtained online.

The reason the technique will not work for undiluted reactor liquid is detailed in the cited reference. In brief, at high concentrations of monomer and polymer, the total scattering from the solution will usually be dominated by inter-polymer effects, and will not accurately reflect the average molecular mass of the individual polymer chains, which is the desired quantity. Sufficient dilution, in this case, online, insures that the scattering is dominated by the Mw of the polymers, and not inter-polymer effects.

Automatic Characterization of Batch Solutions of Polymer

The two vessel scheme has been used by Strelitzki and Reed (ref. 7) to automate batch characterization of polymer solutions, in conjunction with refractive index, multi-angle LS and viscometric detectors. The advantages over the manual dilution methods have been detailed above.

Determination of the Electroviscous Effect.

Figure 18:
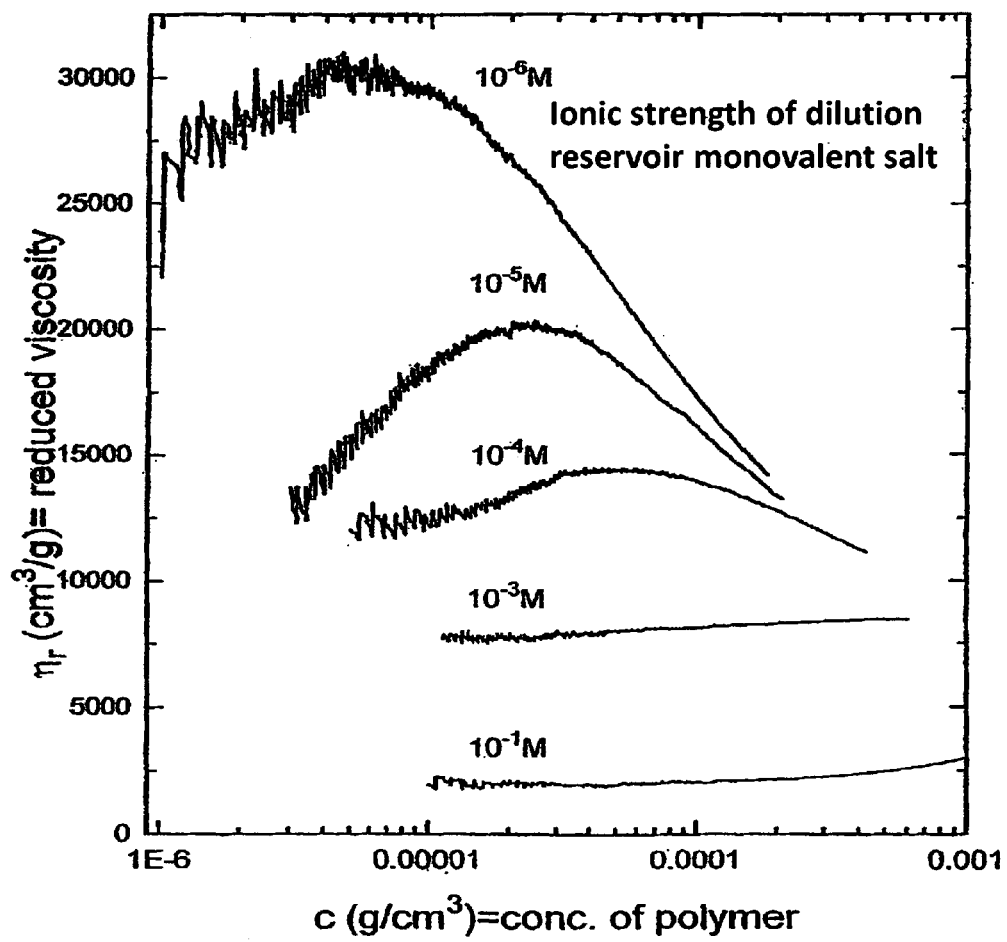
FIG. 18 shows typical online, electroviscous data for hyaluronic acid.

The two vessel scheme has also been used by Strelitzki and Reed (unpublished results) to investigate the electroviscous effect in polyelectrolyte solutions. To accomplish this, polyelectrolytes (hyaluronic acid, xanthan and poly(styrene sulfonate) were used) were dissolved at about 1 mg/ml in a low strength NaCl solution (these generally ran the range from 0M to 0.001M NaCl) and placed in the first vessel. A stock solution of salt at the same concentration as in the first vessel was placed in the second vessel, and the gradient programmer was set to perform a continuous dilution of the polyelectrolyte from its full concentration in the first vessel to zero, or vice versa. Because the original polyelectrolyte solution also contains the counterions of the polyelectrolyte, the actual ionic strength of the solution is higher than the nominal ionic strength due to the added NaCl. As dilution of the polyelectrolyte takes place with pure solvent of the same nominal ionic strength, the total ionic strength of the diluted polyelectrolyte solution actually decreases, since the counterion concentration decreases with dilution, which leads to the electroviscous effect. Typical online, electroviscous data for hyaluronic acid is shown in FIG. 18.

Table of Abbreviations $A_2$ = second virial coefficient (cm$^3$ × Mole/g$^2$)
C = concentration (in g/cm$^3$)
FET = field effect transistor
g/cm$^3$ = grams per cubic centimeter
g/mole = gram per mole
He-Ne laser = Helium Neon laser
HTDSLS = Heterogeneous time dependent static light scattering
HPLC = High Pressure Liquid Chromatography
kD = kiloDalton (1,000 grams per mole)
λ = wavelength
LS = light scattering
M = molarity
$M_w$ = weight average molecular mass (grams per mole)
mg/ml = milligram per milliliter
ml = milliliter
ml/min = milliliter per minute
mV = millivolt
mW = milliwatt
nm = nanometer
PVP = poly(vinyl pyrrolidone)

-continued

Table of Abbreviations $<S^2>$ = mean square radius of gyration (in Angstrom$^2$, nm$^2$, or cm$^2$)
SEC = Size Exclusion Chromatography
SLS = Static light scattering
TDSLS = Time dependent static light scattering
VP = vinyl pyrrolidone

PARTS LIST

The following is a list of parts and materials suitable for use in the present invention:

10 optical assembly of the preferred embodiment of the present invention
20 ring member assembly of a first embodiment of the present invention
21 ring member of the ring member assembly 20 of the first embodiment of the present invention (such as nylon, polycarbonate, anodized aluminum, kevlar or ceramic)
22 chamber of ring member 21
23 incident beam window of ring member 21 (e.g. Edmund scientific borosilicate or sapphire circular windows) (e.g., 5 mm diameter, 2 mm thick)
24 beam dump window of ring member 21 (same as 23, or similar)
31 incident beam (provided by, for example, a vertically polarized 5 mW diode laser commercially available from Lasermax Inc., Rochester, N.Y.)
32 beam dump (such as a window or prism followed by a Rayleigh horn or a detection fiber)
41 optical fibers (such as optical fibers of 100, 150 and 300 micron core diameter, commercially available from Polymicro Technologies as parts FVP100110125, FVP150165180 and FVP300330370, respectively.)
42 holes for optical fibers 41
43 optical harness (e.g. the fibers can be 'braided' together with semiflexible plastic tubes and covered with a rugged sheath, such as is commonly done for telecommunication fiber bundles)
44 ends of the optical fibers 41
45 outer protective sheathing
51 sample solution (for example 1 mg/ml Polyvinylpyrrolidone in water)
52 container for sample solution 51 (glass beaker, for example)
61 handle for ring member assembly 20 (stainless steel, for example)
62 light source (such as a diode laser)
63 converging lens
70 flow mode assembly of the present invention
71 end piece of flow mode assembly 70 (made of nylon, ceramic, anodized aluminum, or kevlar, for example)
72 hydrodynamic tapered flow channels in end pieces 71
73 HPLC tubing and fittings (e.g. Rainin Corp., or ISCO)
74 O-rings
75 retaining bolts
80 fill mode assembly of the present invention
81 base plate (made of plastic or anodized aluminum, for example)
91 sample solution (1 mg/ml polyvinylpyrrolidone in water, for example)
92 container for sample solution 91 (glass, for example)
100 integral chamber assembly of the present invention 101 integral chamber wall (such as stainless steel, black anodized aluminum, ceramic, Teflon, nylon, polycarbonate, or other plastics)
102 integral chamber
111 photodiode assembly (containing Hammamatsu Corp photodiodes, for example)
112 computer for data collection and analysis (such as an IBM personal computer clone such as a Starion 919 from Digital Equipment Corp.)
113 strain relief loop
114 cowl
115 acceptance angle of fiber optic 41 in FIG. 8
116 acceptance angle of fiber optic 41 in FIG. 9 in water
117 acceptance angle of fiber optic 41 in FIG. 9 in toluene
118 optical detectors
161 base plate

REFERENCES

1. Zimm, B. H. *J. Chem. Phys.*, 16, 1093-1116 (1948) (incorporated herein by reference).
2. W. F. Reed "Time-dependent light scattering from singly and multiply stranded linear polymers undergoing random and endwise scission", *J. Chem. Phys.*, 103, 7576-7584, (1995) (incorporated herein by reference).
3. S. Ghosh and W. F. Reed "New Light Scattering Signatures from Polymers undergoing Depolymerization w. App. to Proteoglycan Degradation" *Biopolymers*, 35, 435-450 (1995) (incorporated herein by reference).
4. W. F. Reed "Time-Dependent Processes in Polyelectrolyte Solutions", invited chapter for Berichte der Bunsen-Gesellschaft special volume on Polyelectrolytes, 100, 6, 1-11, 1996 (incorporated herein by reference).
5. Ruth Schimanowski, Roland Strelitzki, David A. Mullin and W. F. Reed "Heterogeneous Time Dependent Static Light Scattering", *Macromolecules*, 32, 21, 7055-7063, 1999 (incorporated herein by reference).
6. Fabio H. Florenzano, Roland Strelitzki and W. F. Reed, "Absolute, Online Monitoring of Polymerization Reactions", *Macromolecules*, vol. 31, no. 21, 7226-7238, 1998 (incorporated herein by reference).
7. Roland Strelitzki and Wayne F. Reed, "Automated Batch Characterization of Polymer Solutions by Static Light Scattering and Viscometry", *J. App. Polym. Sci.*, 73, 2359-2368 1999 (incorporated herein by reference).
8. W. F. Reed, U.S. Pat. No. 6,052,184, "A Miniature, Submersible, Light Scattering Probe for Absolute Macromolecular and Colloidal Characterization".
9. W. F. Reed, "A Method for Online Determination of Polydispersity during Polymerization Reactions", *Macromolecules*, 33, 7165-7172, 2000.
10. A. Giz, H. Giz, J. L. Brousseau, A. Alb and W. F. Reed, "Online Monitoring of a Stepwise Polymerization Reaction: Polyurethane", *J. App. Polym. Sci.*, vol. 82, 2070-2077, 2001.
11. W. F. Reed, "Breaking new ground in polymer science with molecular weight analysis", *American Laboratory*, vol. 32, 16, 20-25, 8/2000.
12. A. Giz, H. Giz, J. L. Brousseau, A. Alb, and W. F. Reed, "Kinetics and Mechanism of Acrylamide Polymerization by Absolute, Online Monitoring of Polymerization Kinetics", *Macromolecules*, vol. 34, 5, 1180-1191, 2001.
13. J. L. Ganter and W. F. Reed, "Real-time Monitoring of Enzymatic Hydrolysis of Galactomannans", *Biopolymers*, vol. 59, 226-242, 2001.
14. Gina A. Sorci and Wayne F. Reed, "Electrostatic and Association Phenomena in Aggregates of Polymers and Micelles", accepted by *Langmuir*, 18, 2, 353-364, 2002.
15. Bruno Grassi, Alina Alb and Wayne F. Reed, "Free radical transfer rate determination using online polymerization monitoring", *Macromolecular Chemistry and Physics*, vol. 202, 12, 2518-2524, 2001.
16. Bruno Grassi and Wayne F. Reed, "Online polymerization monitoring in a continuous tank reactor", *Macromolecular Chemistry and Physics*, 203, 586-597, 2002.
17. Florence Chauvin, Alina Alb, Denis Bertin, and Wayne F. Reed, "Kinetics and molecular weight evolution during controlled radical polymerization", accepted by Macromolecular Chemistry and Physics, 2/20.

All measurements disclosed herein are at standard temperature and pressure, at sea level on Earth, unless indicated otherwise. All materials used or intended to be used in a human being are biocompatible, unless indicated otherwise.

Attached as Appendix A to parent patent application Ser. No. 08/969,386 is data collection and storage software which can be used as a basis for more complex software to perform absolute macromolecular characterization and electronically filter out, count, and characterize large scattering particles.

As used herein, "large scattering particle" (LSP) means an individual particle which would produce scattered light greater than the noise level of the detector (in FIG. 13, for example, the noise level is around 0.04V and the large scattering particles are indicated at about 12 seconds, 26 seconds, 38 seconds, and 46 seconds, in addition to other locations). A LSP could be unwanted impurities, aggregates of the polymer or colloid being studied, or an integral part of the solution.

The detectors and interface operate at a rate fast enough to resolve the residence time of a large scattering particle in the scattering volume. The interface between the photodetector and the computer can be a voltage-converting or a current-converting interface.

Preferably, the scattering volume is chosen such that the number of large scattering particles is small enough to not prevent absolute macromolecular characterization of the substance being studied, and preferably small enough to not significantly interfere with absolute macromolecular characterization of the substance being studied. For example, the average number of LSPs in the scattering volume can be less than 1000, preferably less than 500, more preferably less than 200, even more preferably less than 100, still more preferably less than 50, even more preferably less than 20, even more preferably less than 10, most preferably less than 5. The average number of LSPs in the scattering volume can be even 0 to 1.

The present invention is a relatively inexpensive, simple, versatile apparatus for use in SLS and TDSLS.

The size range of detectability can be, for example, 20 Angstroms to 100 microns. The size range of detectability should run from about 20 Angstroms to 100 microns, with useful measurability in the range from 20 Angstroms to 2 microns, and a preferred range from about 20 Angstroms to 5000 Angstroms. Stated in terms of molar mass, the detectable range of particles should run from about 500 g/mole to 1014 g/mole, with useful measurability in the range of 500 g/mole to $10^9$ g/mole, with a preferred range from about 1000 g/mole to $10^7$ g/mole.

The transmission means for transmitting light from the light detection means to the photodetectors is preferably of a sufficient length and flexibility to allow the submersible probe to be submersed in the fluid to be sampled without submersing the photodetectors, and to allow the other probes to be remote from the photodetectors, which is helpful when the probe is to be used in harsh environments which might damage the photodetectors and associated electronics.

As used in the claims, "light source" can refer to a window, lens, or optical fiber, for letting light in from a light generator, such as a laser.

Novelty of the Apparatus of the Invention Related to Dilution Apparatus

The novelty of one aspect of the present invention consists in providing an automatically and continuously diluted or mixed stream of polymer from polymer-containing vessels whose viscosity is too high to allow current and conventional devices to provide such streams.

While several devices for automatic dilution have been patented, none appear to work over the wide viscosity ranges encountered in the types of polymer systems of main interest in this field. Most that are applicable in the polymer area are more concerned with sampling and diluting relatively low viscosity fluids containing a large amount of particulate matter; e.g. polymer latex, microemulsions, and so on. For example, Garcia-Rubio et al. (U.S. Pat. No. 5,907,108) have disclosed a sampling and dilution system that provides a high degree of dilution, but is oriented towards, e.g. emulsion polymerizations, where reactor fluid viscosity is not high. Other devices include those of Nicoli and Elings (U.S. Pat. No. 4,794,806), which again is oriented towards low viscosity fluids. Bysouth's invention (U.S. Pat. No. 5,801,820) is chiefly concerned with dilution of concentrated, but not viscous, liquids for absorption spectroscopic measurement.

Likewise, commercially available mixing units, such as the ISCO, Waters, and the Dionex, are all incapable of mixing fluids whose viscosities exceed two or three hundred cP. These latter are all piston pumps, which cavitate and lose prime when the fluid viscosity becomes high, and/or bubbles are introduced into their input.

Thus, the current invention fills a need not currently filled by existing patents or commercial devices.

All US patents mentioned herein are incorporated herein by reference.

SPECIFIC EMBODIMENTS

The device consists of the following elements: A pump for withdrawing liquid from the polymer vessel, a pump for withdrawing solvent from a solvent reservoir, a scheme for homogeneously mixing the reactor contents and the solvent, and a means of pumping the mixed solution to the detector train. Often times a secondary dilution stage will be used to achieve even higher levels of dilution than is feasible with a single stage.

Means of withdrawing the liquid from the reactor preferably include, but are not limited to, peristaltic, lobe, gear and screw pumps, and their variants, and certain specialty piston pumps (such as are commercially available from Fluid Metering, Inc. of Syosset, N.Y.). Means of pumping solvent include any of the above mentioned pumps, but also piston and other pumps suitable for pumping low viscosity liquids. Means for homogeneously mixing include micro-mixing 'T' type chambers, actively stirred microchambers, mixing chambers with static mixing elements, or any combination of these. The homogeneously mixed solution can be pumped to the detector train with any of the above mentioned pumps, including the low viscosity handling types, since the mixed solution will be of low viscosity.

The following are possible embodiments.

Recirculating Gear-Pump Based Device:

The gear pump is fed from the reactor by gravity and pumps the reactor liquid at a desired rate, such as 0.1 to 10 ml/minute, and recirculates the majority of the liquid back into the reactor, whereas a small amount is diverted, either continuously or in discrete pulses, towards the mixing chamber. The diversion to the mixing chamber can occur continuously by providing a 'Y' fitting, such that the resistances of the return and mixing chamber feed paths have the desired relationship to feed the mixing chamber at the desired rate. Alternatively the 'Y' fitting can be replaced by a solenoid valve with a diverter outlet, allowing pulses of material to be output to the chamber while the diverter port is electromechanically opened. This solenoid valve would be under the control of a programmable logic controller (PLC).

In turn, the solvent is pumped to the mixing chamber by any type of pump desired, such as a peristaltic pump. The mixing chamber might receive the reactor/solvent flows with partial pre-mix, e.g. by interposing a micro-mixing 'T' between the two pumps and the mixing chamber, or the chamber might accept the flows directly.

The contents of the mixing chamber can feed the detector train directly, or a second dilution stage might be used.

Recirculating Peristaltic Pump Based Device:

When viscosity does not become extremely high it may sometimes be desirable to substitute a peristaltic or other lower viscosity handling pump in place of the gear or screw pump. Two main reasons for doing this are 1) a peristaltic pump can prime itself and withdraw material from a reactor without gravity feed, and 2) the peristaltic pumps are often more economical than gear pumps.

Non-Recirculating Designs.

There are cases where recirculation may not be desired or may not be necessary. In the former category might be found certain high purity products, normally falling under governmental food and drug guidelines, which cannot be re-introduced into a vessel or reactor once withdrawn. In the latter category may fall cases where lag-time is not a critical issue, and many minutes, possibly tens of minutes, constitute acceptable lagtimes. In such cases the mixing chamber can be fed directly by the reactor withdrawal pump, at suitable low flow rates.

Pre-Mixing and Secondary Mixing/Diluting Schemes

Performing pre-mixing can be advantageous in certain circumstances. For example, the reactor may contain highly corrosive materials that should be diluted to a certain level before allowing it to pass through any downstream pumps. Or, a large dilution factor may be desired, in which case large dilutions can be efficiently made as the product of two or more separate dilutions. A predilution scheme allows both low and high pressure mixing, since the first mixing stage can be made at low pressure, exhaling bubbles in the process, and a second stage mixing can be done at high pressure. Also, predilution can in some instances reduce lag-time, especially if the low pressure mixing chamber is allowed to fill more rapidly than it is pumped out by the detector feed pump. In this case, there will normally be an overflow of mixing chamber liquid to waste.

Y-Diversion Scheme Versus Solenoid Valve Diversion Scheme

The 'Y'-diversion scheme is based ideally on Poisseuille's law which states that the flow rate Q of a liquid of viscosity $\eta$ through a pressure drop $\Delta P$ along a capillary of radius R and length L, is given by $$Q = \frac{\pi R^4 \Delta P}{8L\eta}$$

The pressure difference for each outlet side of the L is the pump output pressure minus the outlet pressure of the side. The capillaries can be represented as two resistors in parallel, which divide the flow rate of the pump outlet. For the case where both the mixing chamber and the reactor return are at atmospheric pressure $\Delta P$ is the same and so the relative flow rates are determined simply by L and R of each capillary. In all cases, the ratios of the two resistances is independent of the changing reactor viscosity $\eta$, which ensures a constant flow rate of reactor liquid to the mixing chamber. The over-riding advantage of this method is its simplicity, as it eliminates an electromechanical device (the solenoid valve), which should give it greater reliability in harsh environments, such as near industrial reactors. Its drawback is that the ratio of flow rates of recirculation to chamber is fixed, and hence not changeable by programming. On the other hand, the absolute flow rate to the mixing chamber can be changed simply by changing the gear pump flow rate. Deviations from Poisseuille's law can be corrected empirically. At any rate, it is expected that the ratio of recirculation to chamber feed flow rates will be measured.

Mixing Chamber Considerations

ACOMP experiments have demonstrated the deleterious effects of bubbles entering the detector train. In fact, bubbles in the detector train must be avoided at all cost if reliable operation and online analysis is to be maintained. The best safeguard against bubbles is to perform the mixing of reactor liquid and solvent at low pressure, so that the bubbles are exhaled and vented to atmosphere, thus never entering the pump line to the detectors.

The mixing chamber itself can be of the active or passive type. In either case, reactor fluid and solvent are led into the chamber by tubing, either individually, or pre-mixed, where mixing and any exhalation of bubbles takes place. An active mixer employs a means of stirring, for example any sort of micro-propeller mounted on a rotating shaft. Heating is optional. The mixed fluid is automatically withdrawn from the chamber and pumped through the detector train.

In a passive mixing chamber the reactor fluid and solvent are led in either separately, or pre-mixed, and the static mixing elements in the chamber ensure that mixing occurs.

Optionally, the mixing chamber can have a level sensor, which, when coupled to a PLC will maintain a steady level. A simpler embodiment is to simply equip the chamber with an overflow outlet to waste, for maintaining a given level.

Lag-Time and Response Time Considerations

Inevitably, there is a lag-time between the reactor and the detectors. Normally, a lag-time of up to several minutes is quite acceptable, both for laboratory and plant-level ACOMP. The length of the lag-time is purely a question of pump, chamber and tubing volumes, and flow rates. In principle it can be made almost arbitrarily small. For example, in a recirculating system, fresh material can be continuously circulated to the diversion (of either 'Y' or solenoid types) at a rate of several ml/min. This means that fresh reactor fluid presents itself to the diversion within seconds of withdrawal from the reactor. If the tubing connection to the chamber has low dead volume (e.g. a few tens of microliters), then the fresh reactor liquid will enter the chamber within seconds of reaching the diversion. The time from the mixing chamber to the detectors can likewise be on the order of seconds, so that the entire lag-time can easily be kept under one minute.

The net dead volume from the diversion to the detectors will determine the system response time, the dead volume of the mixing chamber being the single largest source. Since the average, ideal residence time is mixing chamber volume divided by the flow rate of withdrawal from the chamber, the response time can be kept low. For example, withdrawing from a 0.5 ml chamber at a rate of 2 ml/min gives a 15 second response time. The response time sets the minimum time interval over which a change in the state of reactor fluid can be measured, whereas the lag-time is the delay between sampling an instantaneous state and making a measurement on it.

Conditioning Stages:

Because this device is designed to work on a wide variety of polymeric and colloidal fluids, it will be desirable in certain instances to provide further sampling conditioning before the diluted fluid enters the detection train. Examples follow:

Debubbling. This is one of the most common forms of sample conditioning, and is most easily accomplished by providing a micro-mixing chamber vented to atmospheric pressure, so that bubbles are exhaled.

Monomer and other small molecule evaporation. There will be times when it is not desirable to have monomer in the dilution stream along with polymer. An example is the case where there is not a significant spectroscopic difference between the monomer and polymer, so that the relative concentrations are not easily determined. Because of the small volumes used by the device it is easy to provide a small, heated, vented chamber for rapid evaporation of small molecules either before or after the dilution stage.

Breaking self-organizing microstructures. For monitoring inhomogeneous phase reactions, such as those occurring in self-organizing microstructures (SOM) like microemulsion or micellar polymerization, it will be necessary to release the contents of the SOM into the diluted sample stream. This might occur by changing the solvent polarity, ionic content, hydrophobicity, etc. in a conditioning module.

Filtration. Many reactors have large particles, such as microcrystals, microgels, bacteria, aggregates, etc., which are a desired or undesired part of the reaction itself. In many cases it will be necessary to remove such particulates in order for the detector train to function properly. Hence, a filtration device mounted in line with the device may often be required. In some cases hydrophobic or hydrophilic filtration may be used to block a solvent component from entering the detector train.

In some cases filtration may occur after certain detectors but before others. For example, in the Heterogeneous Time Dependent Light Scattering (HTDSLS) case it may be necessary or desirable to let large particles (e.g. up to several microns) pass through the light scattering detector, and possibly also the viscometer. Such particles, however, normally should not be let to flow through the RI and UV detectors, as it might damage them or lead to spurious signals. In such a case, a filter can be placed after the light scattering (and viscometer, if desired) but before the RI and UV detectors.

Sample dissolution. In some cases, e.g. fluidized bed reactors and pressurized vessels producing slurries, the polymer of interest may be produced in particulate or pelletized form. The conditioning stage in this instance would dissolve the solid or slurry material prior to or simultaneously to diluting it with solvent.

Figure 19:
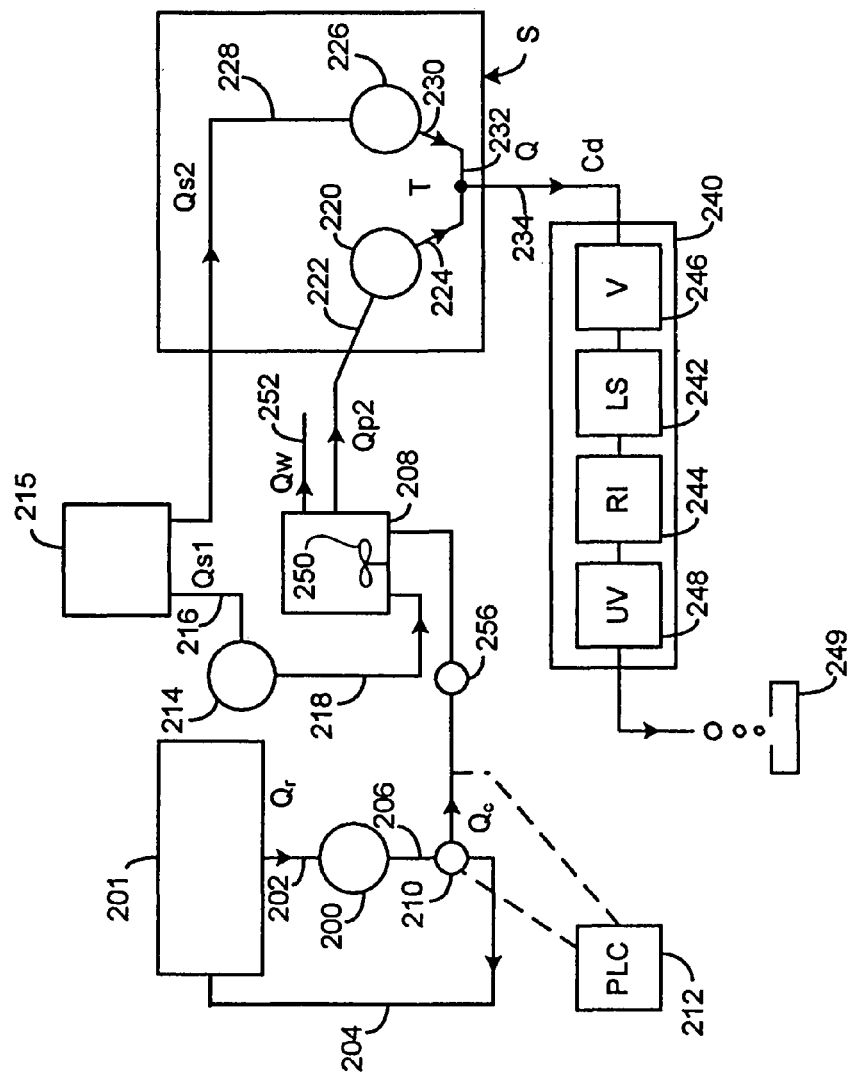
FIG. 19 shows a typical embodiment of the apparatus of the present invention; a two stage, recirculating mixer.

FIG. 19 shows a typical embodiment of the apparatus of the present invention; a two stage, recirculating mixer. A pump (200) is capable of handling high viscosities; pump (200) could be a gear, screw, or lobe pump. In the case of intermediate viscosities a peristaltic pump can also be used. Pump (200) extracts reactor fluid (having a solute concentration Cr)

from reactor (201) via inlet line (202), at a flow rate of Qr. The majority of this flow recirculates back to reactor (201) via recycle line (204), whereas a desired fraction is delivered to the mixing chamber (208) via outlet (206) and/or diverter (210), at an average flow rate of Qc. Diverter (210) can be of either an active or passive type. A passive type can be simply a 'Y', where the lengths and inside diameters of the capillaries going from the 'Y' back to the reactor and into mixing chamber (208) controls the fluid flow split. An active diverter (210) might be a three-way solenoid valve, which normally delivers back to the reactor, but can be actuated by a programmable logic controller (PLC) (212) or similar electronic device, so as to periodically divert flow into mixing chamber (208), to achieve the average Qc. Pump (214) withdraws solvent from a solvent reservoir (215) at a rate Qs1 and delivers it to mixing chamber (208) via outlet (218), where both the reactor fluid and solvent are mixed, yielding a concentration of:

$$Cc = Cr \frac{Qc}{Qc + Qs1}.$$

At this point, a single stage mixer would simply feed the detector train (240) with fluid of concentration Cc, via line (222) and pump (220) at a flow rate Qp2. In the two stage dilutor the compound secondary stage S contains an additional pump (226) that withdraws solvent from the solvent reservoir (215) at a rate Qs2 via line (228). Liquid streams from outlets (224 and 230, respectively) of pumps (220) and (226) are mixed with a very low volume microbore high pressure 'T-type' mixer (232) (e.g. Upchurch, Inc.), for example, or other passive or active mixing device. The flow rate from mixer (232) to detector train (240) via line (234) is hence Q=Qs2+Qp2, and the concentration of solute reaching detector train (240) is $$Cd = Cc \frac{Qp2}{Qp2 + Qs2}$$

In this embodiment, the detector train (240) consists of a single or multi-angle light scattering detector (242) (LS), a refractometer (244) (RI), a viscometer (246) (V), and an ultra-violet/visible spectrophotometer (248) (UV). Other types and combinations of detectors are possible. For example, one or more of these measuring devices could be omitted. Fluid flowing out of detector train (240) goes to waste receptical (249).

A non-recirculating embodiment would simply withdraw reactor fluid at a rate Qc and feed mixing chamber (208) directly. All other flow rates and concentrations remain as stated above. The main difference in this approach is that there will be a longer delay time between the sampling of a fluid element and its measurement by the detector train.

An active mixing element (250) in mixing chamber (208), such as a rotary vane turned by a miniature motor, is shown in FIG. 19. In the case of low viscosity fluids a passive element may be substituted. Mixing chamber (208) is normally vented to atmosphere so as to allow any bubbles coming from the reactor to be exhaled, and not drawn into the detector stream. An active or passive overflow (252) (O), and/or a level sensor, is preferably included in the apparatus (see FIG. 19). In the latter case, the level sensor will work in conjunction with the PLC (212) to control an active diverter (210). In this case, a solvent recirculation loop may be introduced, whereby a second active diverter, also operated by the PLC (212), will deliver, at intervals, the desired average Qs1. In the case of an active overflow without a level sensor, a certain amount of the mixed fluid in mixing chamber (208) will be pumped away by another low viscosity pump at a rate Qw, such that Qw+Qp2=Qc+Qs1. The volume V, of fluid in mixing chamber (208), together with the combined flow rate Qs1+Qc determines the average residence time $t_r$, (and hence response time of the chamber), of a fluid element in the mixing chamber, according to $$t_r = \frac{V}{Qc + Qs1}$$

$t_r$ sets the lower limit of the time for a reaction to occur that can still be monitored by ACOMP. Typically, $t_r$ is on the order of tens or hundreds of seconds. If the mixing chamber (208) is fed in pulses by an active diverter(s) (204) at intervals of Δt, then the mixing chamber (208) smoothes out the discrete injections of reactor fluid and/or solvent as long as $t_r \gg \Delta t$. Commercial solenoid type diverters typically have response times on the order of milliseconds or tens of milliseconds, so the latter criterion is not hard to satisfy, and so the total solute concentration in mixing chamber (208) can be maintained constant, such that the detector signals do not display peaks or pulsations due to concentration fluctuations in mixing chamber (208).

Notes:

1) Pumps (214, 220, and 226) do not have to pump highly viscous liquids, pump (200) being the only high viscosity pump in the embodiment. Pump (214) does not have to work against any significant back-pressure since mixing chamber (208) is vented to atmosphere, and so a very inexpensive peristaltic, piston, diaphragm, or other type pump can be used. Pumps (220 and 226) must be able to pump the low viscosity, mixed sample fluid against the detector train (240) back-pressure, typically on the order of 20 psi to 1000 psi. Many commercially available piston pumps exist for this application.

2) Conditioning module (256) is shown in the drawing, in line with outlet (206) of pump (200). It can perform functions such as heating the reactor fluid to evaporate solvent and/or monomer, or filtering the reactor fluid. Conditioning module (256) can also be place at other points in the diagram, such as at the outlet (218) of mixing chamber (208).

Preliminary Data:

I) Non-Recirculating, Two Stage Mixer with a Peristaltic Pump for Pump (200).

Figure 20:
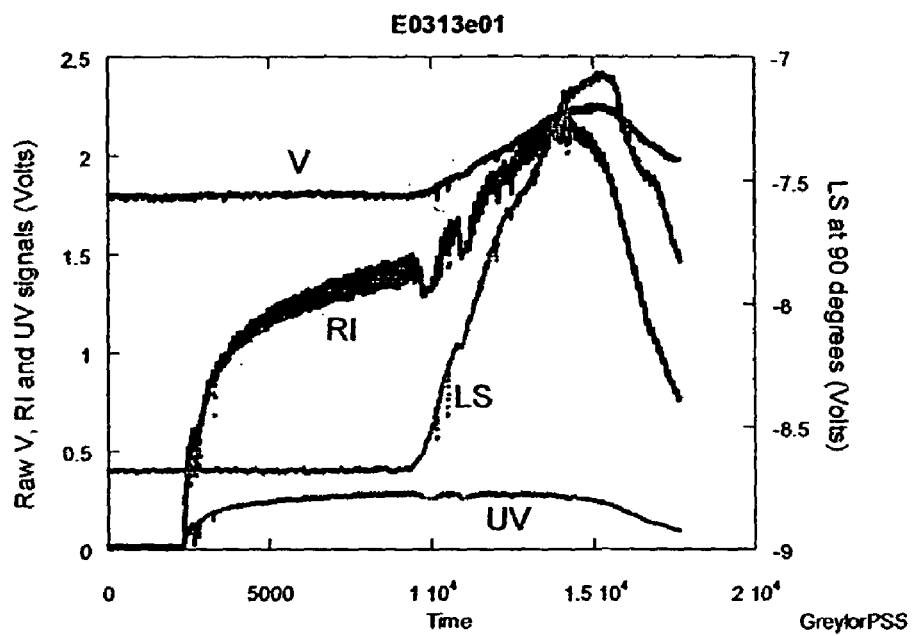
FIG. 20 shows data from a styrene polymerization reaction, using a Greylor peristaltic pump.

In this experiment (results shown in FIG. 20) a Greylor peristaltic pump (Qc=0.08 ml/min) withdrew reactor fluid from a polystyrene polymerization reaction to feed the mixing chamber. In this reaction, 94% by weight styrene was mixed with 6% by weight ethylbenzene, and a free radical initiator (Luperox TAEC, Atofina), was used at 517 ppm, and the reaction was carried out at 117° C. A second Greylor pump, operating at Qs1=0.8 ml/min was used to feed solvent (tetrahydrofuran, or THF) to the mixing chamber. The solvent pump and the pump exiting the mixing chamber were both Agilent 1100 isocratic HPLC (high pressure liquid chromatography) pumps. Qp2 was set at 0.2 ml/min, and Qs2 at 1.8 ml/min, so that Q=2.0 ml/min, feeding the detector train with a solute concentration of approximately Cd=0.01 g/cm$^3$; i.e. roughly a 100 fold dilution. The reaction proceeded until the final viscosity was several thousand cP.

The mixing chamber was a 2 cm diameter scintillation vial atop a magnetic stirrer. A magnetic stir bar in the vial provided the mixing action. A vented cap was made for the vial which held the tubes providing Qc, Qs1, Qw, and Qp2.

The detector train consisted of a homebuilt, single capillary viscometer V, a prototype multi-angle light scattering unit of the inventor's design (U.S. Pat. No. 6,052,184), a Waters 410 RI detector, and a Shimadzu SPD-10AV UV detector. These instruments and methods have been previously described (see endnotes 1-13).

Over the first 2500 s pure THF flowed through the system and established the baseline of each detector. At 2500 s Cd of unreacted styrene in the detector began to flow. The increase in UV and RI signals show the arrival of styrene in the THF at the detector train. The viscosity and light scattering (90 degree signal shown, data from six other angles were simultaneously collected) do not respond to the monomeric styrene. Initiator was added at about 8,500 s. At 10,000 s the beginning of the polymerization is seen via the increase in light scattering and viscosity. At the end of the reaction the fall off in each of the detector signals show that the reactor fluid viscosity due to the polystyrene produced is too high for the pump. The delay time in this configuration was quite long, and was estimated at about 20 minutes.

II) Non-Recirculating, Two Stage Mixer with a Gear Pump.

Figure 21:
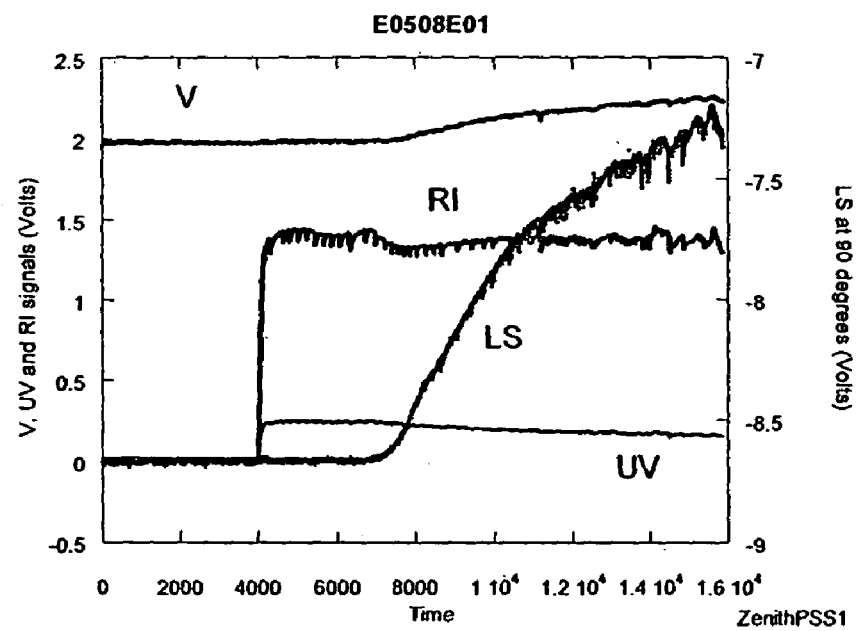
FIG. 21 shows data from a styrene polymerization reaction, using a custom-built Zenith Corporation gear pump.

The second experiment shown here (see FIG. 21) was also a styrene polymerization reaction, under the same conditions as the first. The main difference was the use of a custom-built Zenith Corporation gear pump (with stepper motor drive) for pumping the reaction mixture into the mixing chamber.

The results of the gear pump are clearly superior to those from the peristaltic pump. The RI signal was much more steady, showing the ability of the gear pump to pump the higher viscosities, and the ability of the mixing chamber to deliver a smooth, well-mixed fluid. Even at the highest viscosities the gear pump continued to deliver reactor fluid to the mixing chamber, whereas the peristaltic pump lost its ability to pump. The delay time with the gear pump was substantially lower, on the order of 5 minutes.

Another example of data collected using the same pumping scheme shown for the polystyrene data above is now given. The reaction was a free radical polymerization of two water soluble vinyl polymers at a high weight concentration in pure water. The starting viscosity was around that of water. By the end of the polymerization the viscosity in the reactor was over 100,000 times greater than that of water. The flow rate was 2.0 ml/minute. A 50-fold dilution of the reactor contents occurred in the low pressure mixing chamber, and a subsequent 10-fold dilution in the high pressure mixing chamber.

Figure 22:
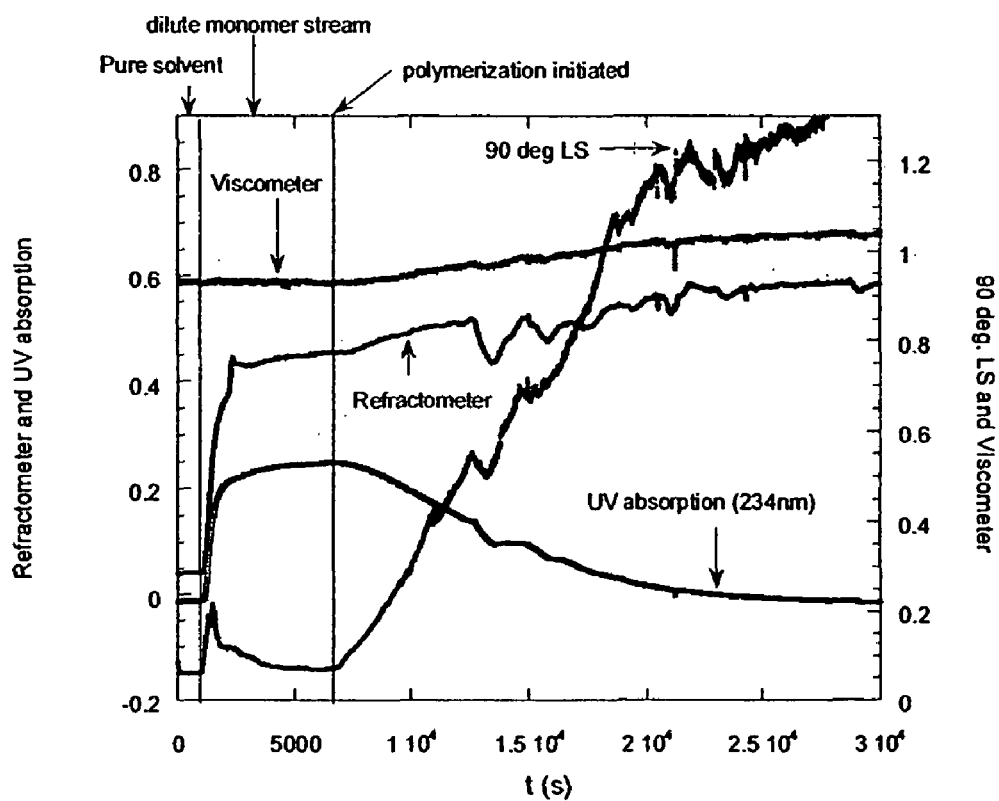
FIG. 22 shows raw data for the reaction from the detector train.

FIG. 22 shows raw data for the reaction from the detector train, consisting of a homebuilt viscometer, a Brookhaven Instruments BI-MwA seven angle light scattering detector, a Shimadzu ultra-violet absorption spectrometer (UV) set to 234 nm, and a Waters 410 refractive index detector.

Pure solvent (water) flows through the detector train initially, after which the diluted monomer stream flows, up until about 7,000 s, at which point the results of initiating the polymerization about 15 minutes earlier (15 minutes is the approximate delay time from reactor to detector train) are seen. The 90 degree light scattering (LS) data are shown (data from the other six angles are not shown), which reflects the increasing concentration of polymer as the monomer is converted during the reaction. The refractometer rises modestly during the reaction, reflecting the fact that the differential index of refraction of the polymer is greater than that of the monomer. The decay of the ultra-violet absorption at 234 nm directly measures the conversion of the monomer, since the absorption is due to the double bond in the monomer, which is lost once incorporated into the polymer, and the absorption is lost. The rise in the viscometer shows the increase in polymer concentration. These raw data were evaluated according to the methods of Florenzano et al. (Ref. 6).

Figure 23:
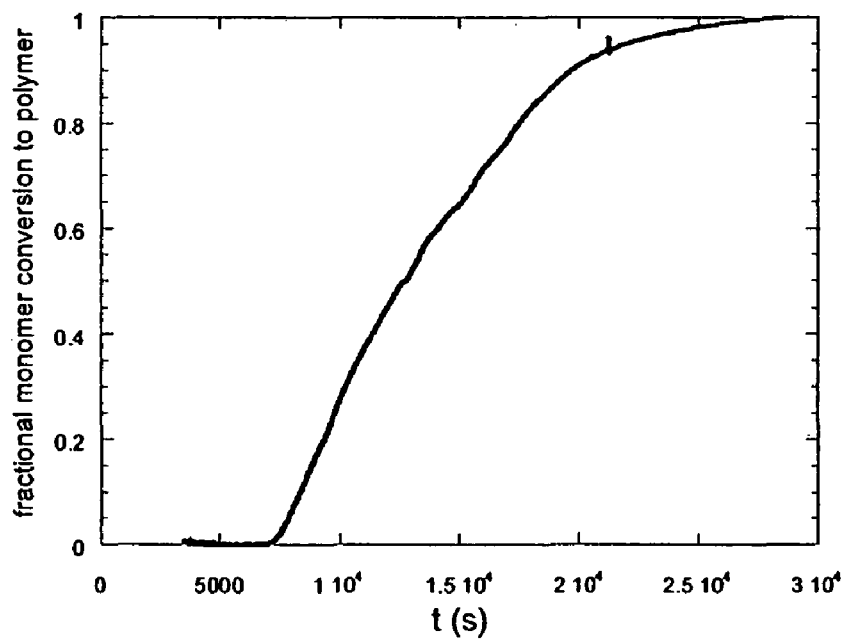
FIG. 23 shows the fraction of monomer converted as a function of time.

FIG. 23 shows the fraction of monomer converted as a function of time. Full conversion of monomer occurs by the end of the reaction.

Figure 24:
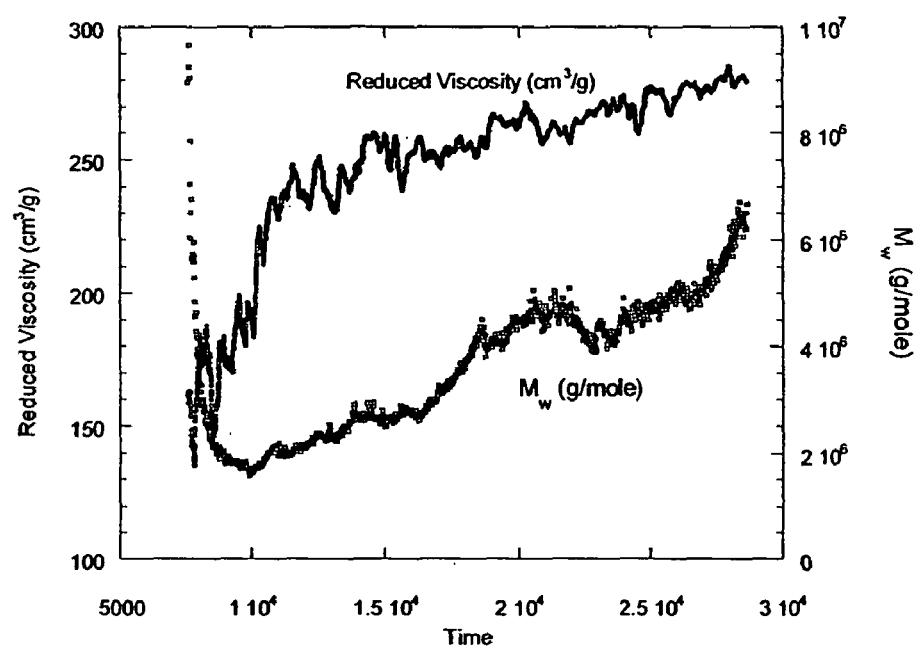
FIG. 24 shows the reduced viscosity of the polymer, and the weight averaged polymer mass $M_w$.

FIG. 24 shows the reduced viscosity of the polymer, and the weight averaged polymer mass $M_w$. Because the solution is so dilute in the detector train (0.0004 g/ml), the reduced viscosity measured is very close to the value of the intrinsic viscosity (e.g. see Grassl and Reed, Ref. 16), which is purely a characteristic of the individual polymer chains' mass, conformation, and hydrodynamic interaction with the solvent (water). It is seen that both $M_w$ and reduced viscosity increase during the reaction, although with different trends. This reflects the fact that $M_w$ and reduced viscosity have separate functional relationships to the polymer population's mass distribution. It is also noted that these quantities, which measure their respective averages of the entire polymer population at any instant during conversion, need not increase (Ref. 8 and 12).

Examples of polymerization reactions and dilution solvents are as follows.

Typical solvents which can be used for dilution include, but are not limited to: water and other aqueous solvents such as those containing simple and complex electrolytes and buffering agents. Also a wide variety of non-aqueous solvents, toluene, chloroform, tetrahydrofuran, butyl acetate, dimethyl sulfoxide, ether, methanol, ethanol, other alcohols, ethylene glycol, n-methylpyrrolidone, etc., as well as mixtures of such solvents.

Typical polymer reactions that can be monitored by ACOMP include:

1) Chain growth reactions, such as those initiated by free radicals, or in anionic, controlled radical, atom transfer radical, and other polymerization reactions, to produce such polymers as polystyrene, polyacrylamide, poly(vinylpyrrolidone), poly(butyl acrylate), etc.

2) Step growth reactions, such as those used to produce such polymers as polyurethane, polyamines, nylons, etc.

3) Polymerization reactions wherein copolymers are formed, whether such copolymers consist of two or more comonomers, and whether they are formed as strictly alternating, random, blocks, grafts, etc.

4) Polymerization reactions in which a pre-dissolution stage may be necessary as part of the conditioning system. Such examples may include cases where there is a slurry formed, such as from a high pressure or phase separating reactor, or solid polymer pellets are formed, such as from a fluidized bed reactor.

5) Polymerization reactions whether they occur in batch or continuous reactors.

6) Degradation reactions in which agents such as acids, bases, ultrasound, enzymes, heat, radiation, etc. degrade biological polymers such as polysaccharides, proteins, and nucleic acids, or synthetic polymers, such as those mentioned above.

'Computer' used throughout the description of this invention refers to any device capable of receiving signals from detectors described herein, and performing the required data reduction and analysis on these signals. Hence, 'computer' can refer to any commercially available computer (e.g. such as those sold by IBM, Dell, Apple, etc.), including workstations (e.g. Sun Microsystems), as well as any microprocessor-based device whether commercially available or designed specifically for the data acquisition and analysis functions described herein.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. An automatic sampling and dilution apparatus for use in a polymer analysis system that includes a flow-through detector capable of transmitting an output signal that is related to a physical parameter of a polymer-containing liquid flowing through the detector, and a device for receiving the output signal, such as a recording and/or display device, the apparatus comprising:
   (a) a primary mixing chamber comprising an active mechanical mixing device within the primary mixing chamber;
   (b) a primary pump capable of continuously withdrawing a variable viscosity liquid from a reactor at a selectable, fixed withdrawal rate over a varying viscosity range of about 50 to about 5,000,000 centipoise (cP), the primary pump comprising an inlet line for transporting the variable viscosity polymer-containing liquid into the primary pump, and an outlet line in fluid-flow relation with the primary mixing chamber for continuously conveying the variable viscosity polymer-containing liquid into the primary mixing chamber;
   (c) a first dilution pump comprising an inlet line for transporting a first dilution solvent from a first solvent reservoir into the first dilution pump, and an outlet line in fluid-flow relation with the primary mixing chamber for continuously delivering the first dilution solvent into the mixing chamber at a selectable, fixed flow rate to mix with the variable viscosity liquid in the mixing chamber, and thereby form a diluted polymer-containing liquid therein; and
   (d) a secondary pump comprising an inlet line in fluid-flow relation with the mixing chamber for continuously conveying the diluted polymer-containing liquid from the mixing chamber into the secondary pump, and an outlet for delivering the diluted polymer-containing liquid into the flow-through detector.

2. The apparatus of claim 1 wherein the primary pump is selected from the group consisting of a gear pump, a lobe pump, and a screw pump.

3. The apparatus of claim 1 wherein the primary mixing chamber includes a vent to maintain the pressure in the primary mixing chamber at ambient atmospheric pressure.

4. The apparatus of claim 1 wherein the primary mixing chamber includes a volume control device for maintaining a selected liquid volume within the primary mixing chamber.

5. The apparatus of claim 1 further comprising a recycle line in fluid-flow relation with the primary pump, the reactor, and the primary mixing chamber, the recycle line, in conjunction with the pump, being capable of maintaining a continuous flow of variable viscosity polymer-containing liquid out of and back into the reactor, and diverting a selected fraction of the continuous flow into the primary pump mixing chamber.

6. The apparatus of claim 1 further comprising:
   (e) a secondary mixing chamber between the primary mixing chamber and the flow-through detector, wherein the secondary mixing chamber is in fluid-flow relation with the outlet line of the secondary pump to receive the diluted polymer-containing liquid from the secondary pump, and including an outlet for connection to the flow-through detector; and
   (f) a second dilution pump including an inlet line for transporting the first dilution solvent from the first solvent reservoir into the second dilution pump, and an outlet line in fluid-flow relation with the secondary mixing chamber to convey the first dilution solvent into the secondary mixing chamber to mix with the diluted polymer-containing liquid and form an ultimate diluted polymer-containing liquid therein.

7. A polymer analysis system comprising the apparatus of claim 1, a flow-through detector in fluid-flow relation with the outlet of the secondary pump for receiving the diluted polymer-containing liquid and for measuring a physical parameter of the diluted polymer-containing liquid flowing through the detector, and a recording device operably connected to the flow-through detector for receiving an output signal from the flow-through detector.

8. The apparatus of claim 1 further comprising a conditioning module in line with the outlet line of the primary pump and adapted to heat the polymer-containing liquid to evaporate solvent, monomer or a combination thereof present in the liquid, or to filter the liquid.

9. A polymer analysis system comprising:
   (a) a primary mixing chamber comprising an active mechanical mixing device within the primary mixing chamber;
   (b) a primary pump capable of continuously withdrawing a variable viscosity liquid from a reactor at a selectable, fixed withdrawal rate over a varying viscosity range of about 50 to about 5,000,000 centipoise (cP), the primary pump comprising an inlet line for transporting the variable viscosity polymer-containing liquid into the primary pump, and an outlet line in fluid-flow relation with the primary mixing chamber for continuously conveying the variable viscosity polymer-containing liquid into the primary mixing chamber;
   (c) a first dilution pump comprising an inlet line for transporting a first dilution solvent from a first solvent reservoir into the first dilution pump, and an outlet line in fluid-flow relation with the primary mixing chamber for continuously delivering the first dilution solvent into the primary mixing chamber at a selectable, fixed flow rate to mix with the variable viscosity fluid in the primary mixing chamber, and thereby form a diluted polymer-containing liquid therein;
   (d) a secondary pump comprising an inlet line in fluid-flow relation with the primary mixing chamber for continuously conveying the diluted polymer-containing liquid from the primary mixing chamber into the secondary pump, and an outlet; and
   (e) a flow-through detector in fluid-flow relation with the outlet of the secondary pump for receiving the diluted polymer-containing liquid, and for measuring a physical parameter of the diluted polymer-containing liquid flowing through the detector, the flow-through detector being capable of transmitting to a recording device an output signal.

10. The polymer analysis system of claim 9 wherein the primary pump is selected from the group consisting of a gear pump, a lobe pump, and a screw pump.

11. The polymer analysis system of claim 9 wherein the primary mixing chamber includes a vent to maintain the pressure in the primary mixing chamber at ambient atmospheric pressure, and a volume control device for maintaining a selected liquid volume within the primary mixing chamber.

12. The polymer analysis system of claim 9 wherein the flow-through detector comprises a light scattering detector.

13. The polymer analysis system of claim 9 wherein the flow-through detector comprises a plurality of flow-through detectors.

14. The polymer analysis system of claim 9 wherein the flow-through detector comprises a light scattering detector and a concentration detector.

15. The polymer analysis system of claim 9 wherein the flow-through detector comprises a light scattering detector, a concentration detector, and a viscometric detector.

16. The polymer analysis system of claim 9 further comprising a recording device operably connected to the flow-through detector for receiving and recording the output signal from the flow-through detector.

17. The polymer analysis system of claim 16 wherein the recording device comprises a microprocessor for receiving the output signal from the flow-through detector and for calculating therefrom a property of the variable viscosity polymer-containing liquid.

18. The apparatus of claim 17 wherein the property comprises a molecular weight parameter of a polymer present in the variable viscosity polymer-containing liquid.

19. The apparatus of claim 17 wherein the property comprises a viscometric property of a polymer present in the variable viscosity polymer-containing liquid.

20. The polymer analysis system of claim 17 wherein the property comprises a percentage conversion of monomer-to-polymer for a polymer being formed in the variable viscosity polymer-containing liquid.

21. The polymer analysis system of claim 9 further comprising a recycle line in fluid-flow relation with the primary pump, the reactor, and the primary mixing chamber, the recycle line, in conjunction with the primary pump, being capable of maintaining a continuous flow of variable viscosity polymer-containing liquid out of and back into the reactor, and diverting a selected fraction of the continuous flow into primary mixing chamber.

22. A polymer analysis system comprising:
(a) a primary mixing chamber comprising an active mechanical mixing device within the primary mixing chamber;
(b) a primary pump capable of continuously withdrawing a variable viscosity liquid from a reactor at a selectable, fixed withdrawal rate over a varying viscosity range of about 50 to about 5,000,000 centipoise (cP), the primary pump comprising an inlet line for transporting the variable viscosity polymer-containing liquid into the primary pump, and an outlet line in fluid-flow relation with the primary mixing chamber for continuously conveying the variable viscosity polymer-containing liquid into the primary mixing chamber;
(c) a first dilution pump comprising an inlet line for transporting a dilution solvent from a solvent reservoir into the first dilution pump, and an outlet line in fluid-flow relation with the primary mixing chamber for continuously delivering the dilution solvent into the primary mixing chamber at a selectable, fixed flow rate to mix with the variable viscosity fluid in the primary mixing chamber, and thereby form a diluted polymer-containing liquid therein;
(d) a secondary pump comprising an inlet line in fluid-flow relation with the primary mixing chamber for continuously conveying the diluted polymer-containing liquid from the primary mixing chamber into the pump, and an outlet line;
(e) a secondary mixing chamber including a first inlet in fluid-flow relation with the outlet line of the secondary pump for receiving the diluted polymer-containing liquid from the secondary pump, and also including a second inlet and an outlet;
(f) a second dilution pump including an inlet line for transporting the dilution solvent from the solvent reservoir into the second dilution pump, and an outlet line in fluid-flow relation with the second inlet of the secondary mixing chamber to convey the dilution solvent into the secondary mixing chamber to mix with the diluted polymer-containing liquid and form an ultimate diluted polymer-containing liquid therein; and
(g) a flow-through detector in fluid-flow relation with outlet of the secondary mixing chamber, for receiving the ultimate diluted polymer-containing liquid, and for measuring a physical parameter of the ultimate diluted polymer-containing liquid flowing through the detector, the flow-through detector being capable of transmitting an output signal to a recording device.

23. The polymer analysis system of claim 22 wherein the primary pump is selected from the group consisting of a gear pump, a lobe pump, and a screw pump.

24. The polymer analysis system of claim 22 wherein the primary mixing chamber includes a vent to maintain the pressure in the primary mixing chamber at ambient atmospheric pressure, and a volume control device for maintaining a selected liquid volume within the primary mixing chamber.

25. The polymer analysis system of claim 22 wherein the flow-through detector comprises a light scattering detector.

26. The polymer analysis system of claim 22 wherein the flow-through detector comprises a plurality of flow-through detectors.

27. The polymer analysis system of claim 22 wherein the flow-through detector comprises a light scattering detector and a concentration detector.

28. The polymer analysis system of claim 22 wherein the flow-through detector comprises a light scattering detector, a concentration detector, and a viscometric detector.

29. The polymer analysis system of claim 22 wherein the secondary pump and the second dilution pump each comprise a high pressure liquid chromatography pump.

30. The polymer analysis system of claim 22 further comprising a recycle line in fluid-flow relation with the primary pump, the reactor, and the primary mixing chamber, the recycle line, in conjunction with the primary pump, being capable of maintaining a continuous flow of variable viscosity polymer-containing liquid out of and back into the reactor, and diverting a selected fraction of the continuous flow into the primary mixing chamber.

31. The polymer analysis system of claim 22 further comprising a recording device operably connected to the flow-through detector for receiving and recording the output signal from the flow-through detector.

32. The polymer analysis system of claim 31 wherein the recording device comprises a microprocessor for receiving the output signal of the flow-through detector and calculating therefrom a property of the variable viscosity polymer-containing liquid.

33. The polymer analysis system of claim 32 wherein the property comprises a molecular weight parameter of a polymer present in the variable viscosity polymer-containing liquid.

34. The polymer analysis system of claim 32 wherein the property comprises a viscometric parameter of a polymer present in the variable viscosity polymer-containing liquid.

35. The polymer analysis system of claim 32 wherein the property comprises a percentage conversion of monomer-to-polymer for a polymer being formed in the variable viscosity polymer-containing liquid.

* * * * *

UNITED STATES PATENT AND TRADEMARK OFFICE
CERTIFICATE OF CORRECTION

PATENT NO. : 8,322,199 B2
APPLICATION NO. : 11/706458
DATED : December 4, 2012
INVENTOR(S) : Wayne F. Reed It is certified that error appears in the above-identified patent and that said Letters Patent is hereby corrected as shown below:

IN THE SPECIFICATION:

Column 16, line 59, "1014" should be --$10^{14}$--.

Column 22, line 7, "106" should be --$10^6$--.

Column 23, line 31, "OM" should be --0M--.

Signed and Sealed this
Twenty-second Day of October, 2013

Teresa Stanek Rea
*Deputy Director of the United States Patent and Trademark Office*